(12) United States Patent
Osada et al.

(10) Patent No.: US 10,253,014 B2
(45) Date of Patent: Apr. 9, 2019

(54) CYCLIC AMINE DERIVATIVE AND PHARMACEUTICAL USE THEREOF

(71) Applicant: Toray Industries, Inc., Tokyo (JP)

(72) Inventors: Yuji Osada, Iyo-gun (JP); Naoki Izumimoto, Kamakura (JP); Yasuhiro Morita, Kamakura (JP); Shuji Udagawa, Kamakura (JP); Katsuhiko Iseki, Kamakura (JP); Tomoya Miyoshi, Kamakura (JP); Shunsuke Iwano, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/560,365

(22) PCT Filed: Mar. 24, 2016

(86) PCT No.: PCT/JP2016/059293
§ 371 (c)(1),
(2) Date: Sep. 21, 2017

(87) PCT Pub. No.: WO2016/152952
PCT Pub. Date: Sep. 29, 2016

(65) Prior Publication Data
US 2018/0072701 A1    Mar. 15, 2018

(30) Foreign Application Priority Data

Mar. 24, 2015 (JP) .................... 2015-061249

(51) Int. Cl.
| | | |
|---|---|---|
| C07D 401/06 | (2006.01) | |
| A61K 31/4178 | (2006.01) | |
| A61K 31/454 | (2006.01) | |
| C07D 403/06 | (2006.01) | |

(52) U.S. Cl.
CPC ........ C07D 401/06 (2013.01); A61K 31/4178 (2013.01); A61K 31/454 (2013.01); C07D 403/06 (2013.01)

(58) Field of Classification Search
CPC ............................. C07D 401/06; C07D 403/06
USPC ........................................... 546/210; 548/953
See application file for complete search history.

(56) References Cited

U.S. PATENT DOCUMENTS 9,505,740 B2 * 11/2016 Morita ................. A61K 31/454

FOREIGN PATENT DOCUMENTS

| JP | 2005-507906 A | 3/2005 |
|---|---|---|
| JP | 2005-527519 A | 9/2005 |
| JP | 4563675 B2 | 8/2010 |
| WO | 03/031432 A1 | 4/2003 |
| WO | 2006/137465 A1 | 12/2006 |
| WO | 2013/147160 A1 | 10/2013 |
| WO | 2015/046403 A1 | 4/2015 |

* cited by examiner

*Primary Examiner* — Jeffrey H Murray
(74) *Attorney, Agent, or Firm* — DLA Piper LLP (US)

(57) ABSTRACT

A cyclic amine derivative represented by a general formula (I) or a pharmacologically acceptable salt thereof:

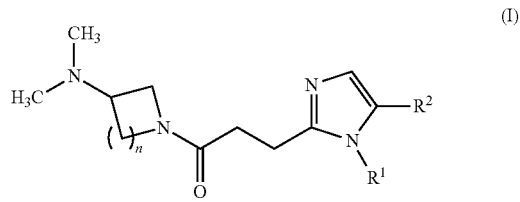

(I)

wherein n represents 1 or 3, $R^1$ represents an alkyl group having 1 to 6 carbon atoms unsubstituted, substituted with a halogen atom or substituted with an alkyloxy group having 1 to 4 carbon atoms and $R^2$ represents a hydrogen atom or a halogen atom.

13 Claims, 12 Drawing Sheets

CYCLIC AMINE DERIVATIVE AND PHARMACEUTICAL USE THEREOF

TECHNICAL FIELD

This disclosure relates to a cyclic amine derivative and pharmaceutical use thereof.

BACKGROUND

Pain is an unpleasant sensory and emotional experience associated with actual or potential tissue damage. Pain is classified according to cause into nociceptive pain, neuropathic pain and psychogenic pain.

Neuropathic pain is pathological pain caused by peripheral or central nervous system dysfunction, more specifically, pain caused by e.g., direct damage and oppression of the nerve tissue despite of no nociceptive stimulus to a nociceptor. As the therapeutic agent for neuropathic pain, an anticonvulsant, an antidepressant, an anxiolytic drug or an antiepileptic drug (gabapentin, pregabalin or the like) is used.

In the meantime, compounds having the structure of a derivative analogous to our compounds as a partial structure are known in Japanese Patent No. 4563675. The possibility that the compounds may have drug efficacy to excessive overweight or obesity is suggested. International Publication WO 2006/137465 discloses that some nitrogen-containing heterocyclic derivatives exert an antagonistic action specific to one of NMDA receptors, i.e., NR1/NR2B receptor. International Publication WO 2013/147160 discloses that imidazole derivatives exert an analgesic action.

However, therapy with a conventional therapeutic agent for neuropathic pain is highly frequently associated with central nervous system adverse effects (e.g., dizziness, nausea or vomiting). Since it is difficult to administer such a therapeutic agent for a long term, development of a novel therapeutic agent for neuropathic pain has been desired.

Whether or not the substituted piperidines described in JP '675 have analgesic action including action against neuropathic pain is not known. Usefulness of the substituted piperidines described in JP '675 as a lead compound for an analgesic agent, particularly a therapeutic agent for neuropathic pain, has not yet been reported. It has been suggested that the nitrogen-containing heterocyclic derivatives described in WO '465 may have usefulness as an analgesic agent. It is disclosed that the imidazole derivatives described in WO '160 have an analgesic action.

It could therefore be helpful to provide a compound having a strong analgesic action for pain, in particular, neuropathic pain.

SUMMARY

We thus provide a cyclic amine derivative having a strong analgesic effect against pain, in particular, neuropathic pain.

More specifically, we provide a cyclic amine derivative represented by general formula (I) or a pharmacologically acceptable salt thereof.

(I)

wherein n represents 1 or 3, $R^1$ represents an alkyl group having 1 to 6 carbon atoms unsubstituted, substituted with a halogen atom or substituted with an alkyloxy group having 1 to 4 carbon atoms and $R^2$ represents a hydrogen atom or a halogen atom.

In the cyclic amine derivative or a pharmacologically acceptable salt thereof, it is preferable that $R^2$ is a hydrogen atom or a chlorine atom. Analgesic action can be enhanced by defining $R^2$ to be a hydrogen atom or a chlorine atom.

In the cyclic amine derivative or a pharmacologically acceptable salt thereof, it is further preferable that $R^1$ is an unsubstituted alkyl group having 1 to 6 carbon atoms. Analgesic action can be further enhanced by defining $R^1$ to be an unsubstituted alkyl group having 1 to 6 carbon atoms.

We also provide a medicine containing a cyclic amine derivative represented by general formula (I), or a pharmacologically acceptable salt thereof as an active ingredient.

The medicine is preferably an analgesic agent, and particularly preferably a therapeutic agent for neuropathic pain.

We further provide a pharmaceutical composition containing a cyclic amine derivative represented by general formula (I) or a pharmacologically acceptable salt thereof and e.g., a pharmacologically acceptable excipient.

We also provide a cyclic amine derivative represented by general formula (I) or a pharmacologically acceptable salt thereof for use as a medicine.

We further provide a cyclic amine derivative represented by general formula (I) or a pharmacologically acceptable salt thereof for use in pain treatment. The pain is preferably neuropathic pain.

We still further provide use of a cyclic amine derivative represented by general formula (I) or a pharmacologically acceptable salt thereof for treating pain. The pain is preferably neuropathic pain.

We yet further provide use of a cyclic amine derivative represented by general formula (I) or a pharmacologically acceptable salt thereof in producing a medicine for treating pain. The pain is preferably neuropathic pain.

We also provide a method of treating pain including administering a therapeutically effective amount of a cyclic amine derivative represented by the above general formula (I) or a pharmacologically acceptable salt thereof to a patient in need thereof. The pain is preferably neuropathic pain.

The cyclic amine derivative or a pharmacologically acceptable salt thereof has a strong analgesic effect against pain, in particular, neuropathic pain.

DETAILED DESCRIPTION

Figure 1:
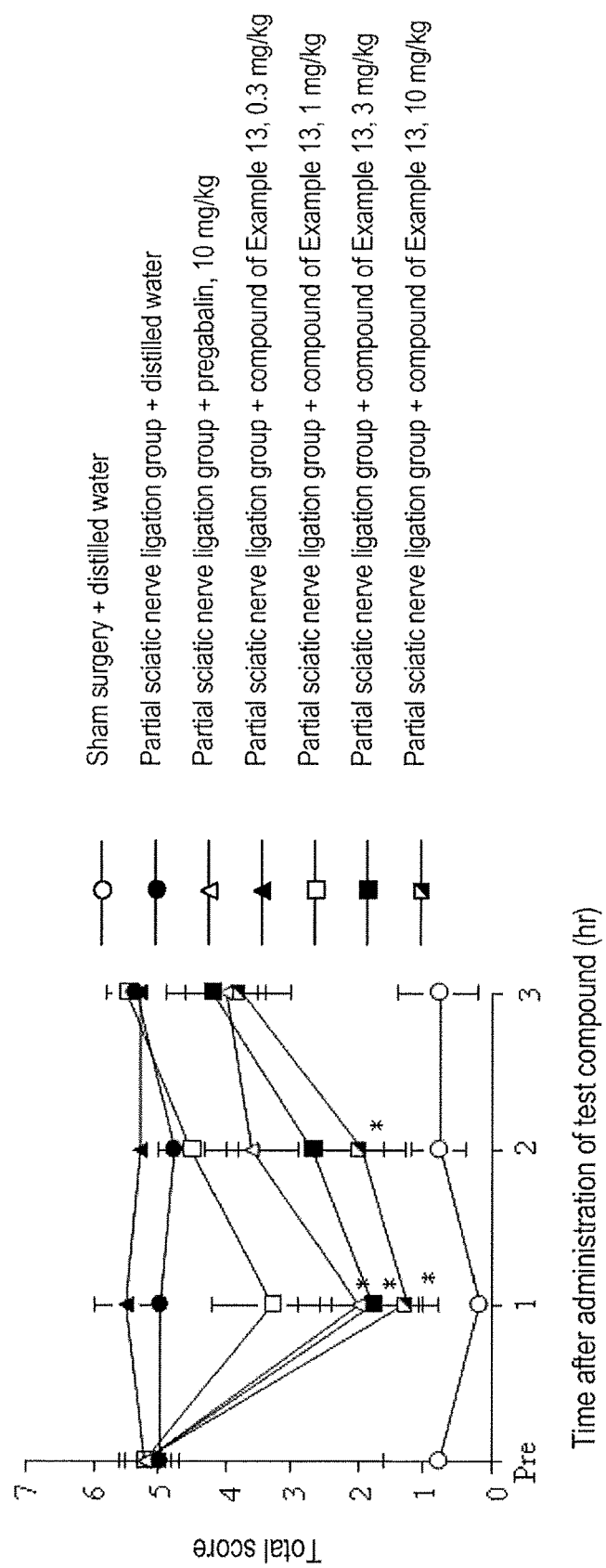
FIG. 1 is a graph showing the effect of the compound of Example 13 in a mouse partial sciatic nerve ligation model (oral administration).

The following terms are, unless otherwise specified, defined as follows.

Our cyclic amine derivative is represented by general formula (I).

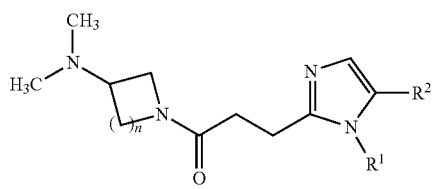

wherein n represents 1 or 3, $R^1$ represents an alkyl group having 1 to 6 carbon atoms unsubstituted, substituted with a halogen atom or substituted with an alkyloxy group having 1 to 4 carbon atoms and $R^2$ represents a hydrogen atom or a halogen atom.

In an example of the cyclic amine derivative, n represents 1, $R^1$ represents an alkyl group having 1 to 6 carbon atoms unsubstituted, substituted with a fluorine atom or substituted with an alkyloxy group having 1 to 4 carbon atoms and $R^2$ represents a hydrogen atom or a halogen atom.

In an example of the cyclic amine derivative, n represents 1, $R^1$ represents an alkyl group having 1 to 6 carbon atoms unsubstituted, substituted with a fluorine atom or substituted with an alkyloxy group having 1 to 4 carbon atoms and $R^2$ represents a hydrogen atom or a chlorine atom.

In an example of the cyclic amine derivative, n represents 1, $R^1$ represents an alkyl group having 1 to 6 carbon atoms unsubstituted, substituted with a fluorine atom or substituted with an alkyloxy group having 1 carbon atom and $R^2$ represents a hydrogen atom or a chlorine atom.

In an example of the cyclic amine derivative, n represents 1, $R^1$ represents an alkyl group having 1 to 3 carbon atoms unsubstituted, substituted with a fluorine atom or substituted with an alkyloxy group having 1 carbon atom and $R^2$ represents a hydrogen atom or a chlorine atom.

In an example of the cyclic amine derivative, n represents 1, $R^1$ represents an unsubstituted alkyl group having 1 to 6 carbon atoms and $R^2$ represents a hydrogen atom or a chlorine atom.

In an example of the cyclic amine derivative, n represents 1, $R^1$ represents an unsubstituted alkyl group having 1 to 3 carbon atoms and $R^2$ represents a hydrogen atom or a chlorine atom.

In an example of the cyclic amine derivative, n represents 3, $R^1$ represents an alkyl group having 1 to 6 carbon atoms unsubstituted, substituted with a fluorine atom or substituted with an alkyloxy group having 1 to 4 carbon atoms and $R^2$ represents a hydrogen atom or a halogen atom.

In an example of the cyclic amine derivative, n represents 3, $R^1$ represents an alkyl group having 1 to 6 carbon atoms unsubstituted, substituted with a fluorine atom or substituted with an alkyloxy group having 1 to 4 carbon atoms and $R^2$ represents a hydrogen atom or a chlorine atom.

In an example of the cyclic amine derivative, n represents 3, $R^1$ represents an alkyl group having 1 to 6 carbon atoms unsubstituted, substituted with a fluorine atom or substituted with an alkyloxy group having 1 carbon atom and $R^2$ represents a hydrogen atom or a chlorine atom.

In an example of the cyclic amine derivative, n represents 3, $R^1$ represents an alkyl group having 1 to 3 carbon atoms unsubstituted, substituted with a fluorine atom or substituted with an alkyloxy group having 1 carbon atom and $R^2$ represents a hydrogen atom or a chlorine atom.

In an example of the cyclic amine derivative, n represents 3, $R^1$ represents an unsubstituted alkyl group having 1 to 6 carbon atoms and $R^2$ represents a hydrogen atom or a chlorine atom.

In an example of the cyclic amine derivative, n represents 3, $R^1$ represents an unsubstituted alkyl group having 1 to 3 carbon atoms and $R^2$ represents a hydrogen atom or a chlorine atom.

"Halogen atom" refers to a fluorine atom, a chlorine atom, a bromine atom or an iodine atom.

"Alkyloxy group having 1 to 4 carbon atoms" refers to a group obtained by binding a linear, branched or cyclic saturated hydrocarbon group having 1 to 4 carbon atoms to an oxygen atom. For example, a methoxy group, an ethoxy group, a n-propyloxy group, an isopropyloxy group, a cyclopropyloxy group, a n-butoxy group, a sec-butoxy group or a tert-butoxy group can be mentioned.

"Alkyl group having 1 to 6 carbon atoms unsubstituted, substituted with a halogen atom or substituted with an alkyloxy group having 1 to 4 carbon atoms" refers to a linear, branched or cyclic saturated hydrocarbon group having 1 to 6 carbon atoms unsubstituted, substituted with a halogen atom as mentioned above or substituted with an alkyloxy group having 1 to 4 carbon atoms as mentioned above. For example, a methyl group, an ethyl group, a n-propyl group, an isopropyl group, a cyclopropyl group, a cyclopropylmethyl group, a n-butyl group, a sec-butyl group, a tert-butyl group, a n-pentyl group, an isopentyl group, a n-hexyl group, an isohexyl group, or a cyclohexyl group, or a 2-chloroethyl group, a 2,2-difluoroethyl group, a 2,2,2-trifluoroethyl group, a 2-methoxyethyl group, a 2-ethoxyethyl group or 2-isopropyloxyethyl group can be mentioned.

Specific examples of a preferable compound as a cyclic amine derivative represented by the above will be shown in Tables 1-1 and 1-2. However, this disclosure is not limited to these.

TABLE 1-1
Structural formula
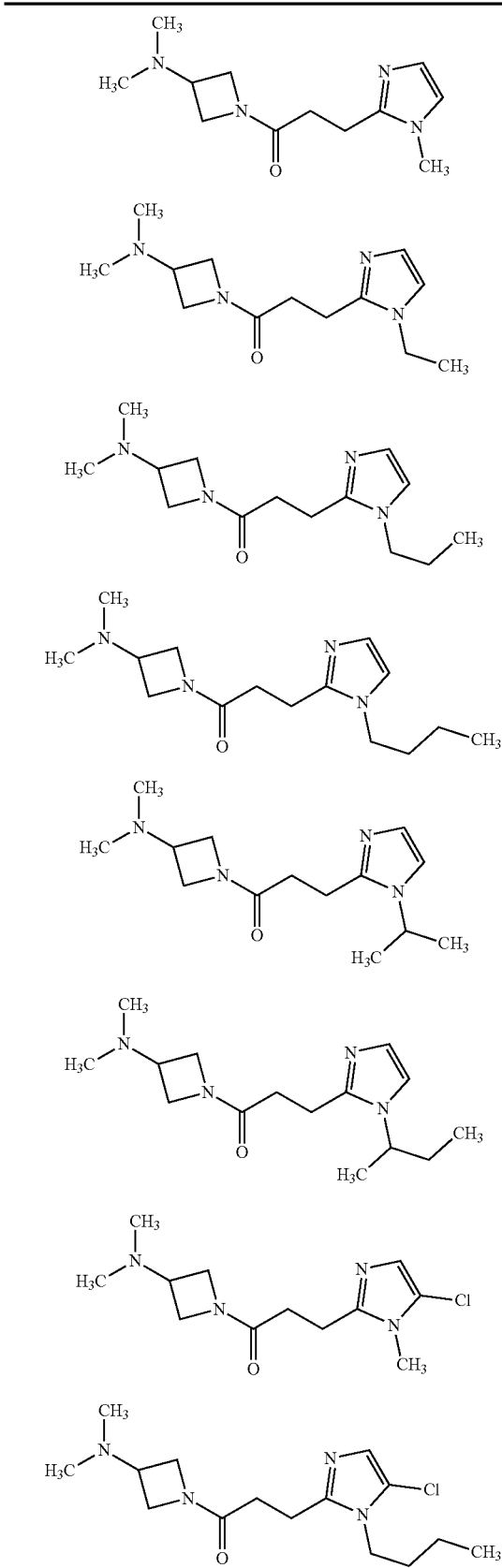
TABLE 1-1-continued
Structural formula
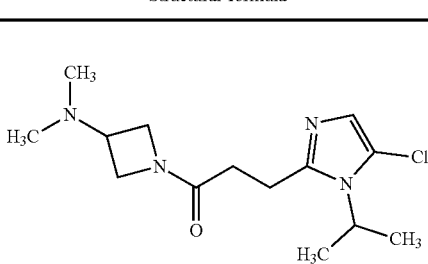
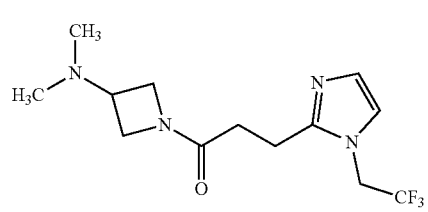 [SMILES: CN(C)C1CN(C(=O)CCc2nccn2CC(F)(F)F)C1]
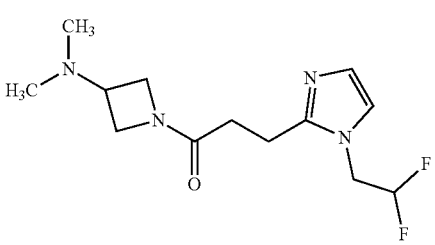 [SMILES: CN(C)C1CN(C(=O)CCc2nccn2CC(F)F)C1]
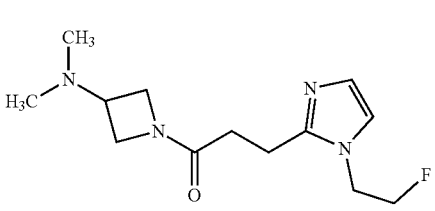 [SMILES: CN(C)C1CN(C(=O)CCc2nccn2CCF)C1]
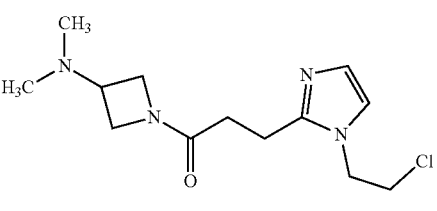 [SMILES: CN(C)C1CN(C(=O)CCc2nccn2CCCl)C1]
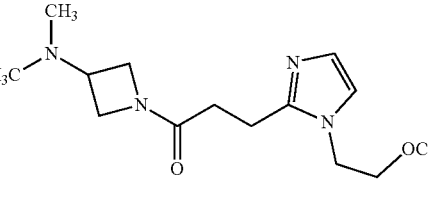
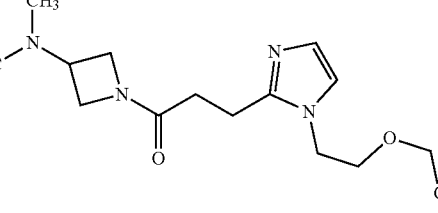

TABLE 1-1-continued
Structural formula
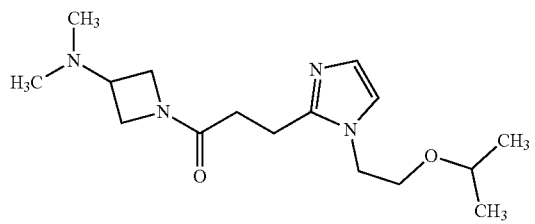 [SMILES: CC(C)OCCn1ccnc1CCC(=O)N1CC(N(C)C)C1]
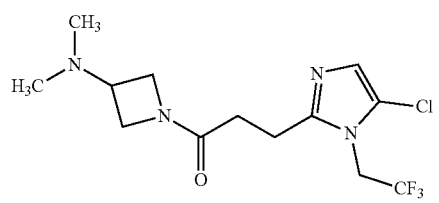 [SMILES: CN(C)C1CN(C(=O)CCc2ncc(Cl)n2CC(F)(F)F)C1]
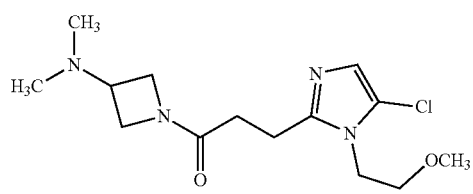 [SMILES: COCCn1c(Cl)cnc1CCC(=O)N1CC(N(C)C)C1]
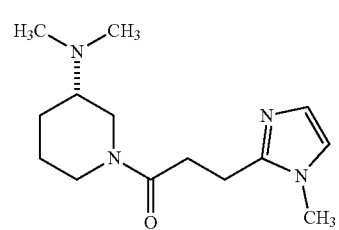 [SMILES: CN(C)[C@H]1CCCN(C(=O)CCc2nccn2C)C1]
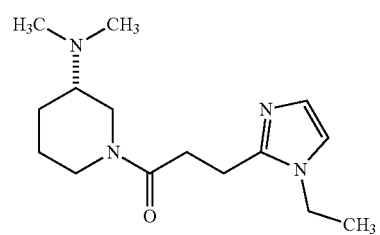 [SMILES: CCn1ccnc1CCC(=O)N1CCC[C@H](N(C)C)C1]
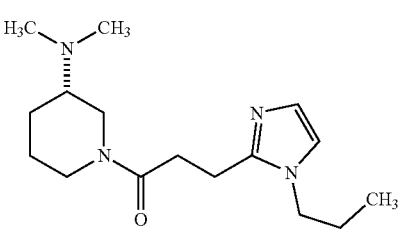 [SMILES: CCCn1ccnc1CCC(=O)N1CCC[C@H](N(C)C)C1]
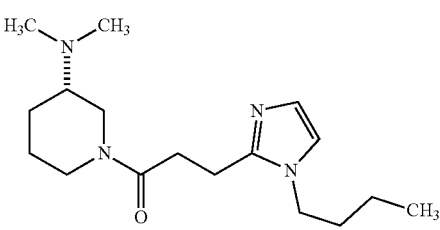
TABLE 1-1-continued
Structural formula
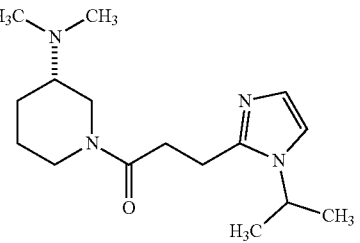
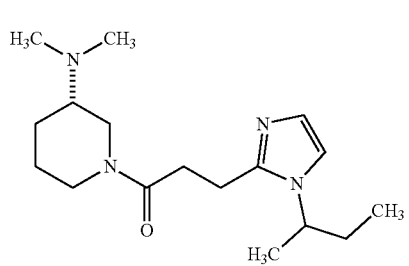 [SMILES: CCC(C)n1ccnc1CCC(=O)N1CCC[C@H](N(C)C)C1]
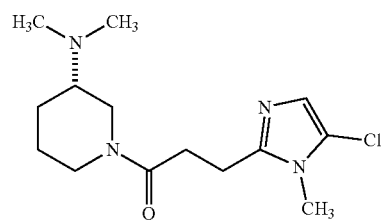 [SMILES: CN(C)[C@H]1CCCN(C(=O)CCc2ncc(Cl)n2C)C1]
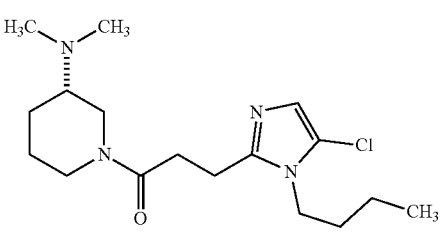 [SMILES: CCCCn1c(Cl)cnc1CCC(=O)N1CCC[C@H](N(C)C)C1]
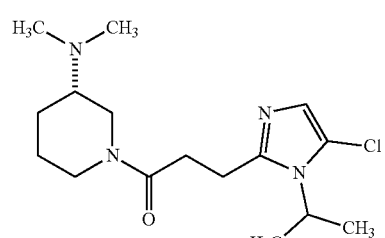
TABLE 1-2
Structural formula
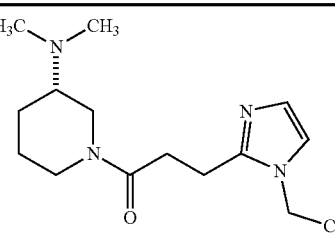

TABLE 1-2-continued

Structural formula (structures only; no transcribable text)

TABLE 1-2-continued

Structural formula

TABLE 1-2-continued

Structural formula

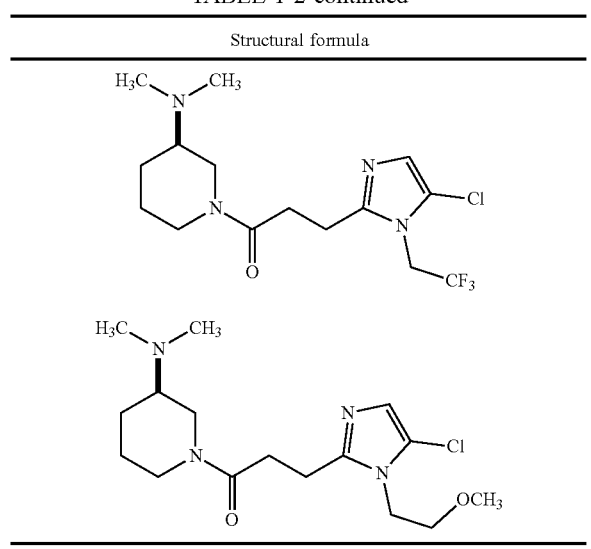

When an asymmetric carbon is present in the cyclic amine derivative, all enantiomers and mixtures of these are included in the cyclic amine derivative. When a stereoisomer is present in the cyclic amine derivative, all stereoisomers and mixtures of these are included in the cyclic amine derivative.

The cyclic amine derivative may be labeled with a radioisotope. Examples of the radioisotope for use in labeling include $^3H$, $^{14}C$ and/or $^{125}I$.

The cyclic amine derivative may be deuterated.

As the pharmacologically acceptable salt of the cyclic amine derivative, for example, an inorganic salt such as a hydrochloride, a sulfate, a phosphate or a hydrobromide; or an organic salt such as an oxalate, a malonate, a citrate, a fumarate, a lactate, a malate, a succinate, a tartrate, an acetate, a trifluoroacetate, a maleate, a gluconate, a benzoate, a salicylate, a xinafoate, a pamoate, an ascorbate, an adipate, a methanesulfonate, a p-toluenesulfonate or a cinnamate. These salts may be present in the form of a hydrate, a solvate or a crystalline polymorph.

The cyclic amine derivative can be synthesized by the production methods that will be described below. Note that, the cyclic amine derivatives obtained by the following production methods each can be isolated/purified by a known means (for example, solvent extraction, recrystallization and/or chromatography) and converted into desired salts by known methods or a similar method thereto. When the cyclic amine derivative is obtained in the form of a salt, it can be converted into a cyclic amine derivative or another desired salt by a known method or a similar method thereto.

1. Production Method for Cyclic Amine Derivative:

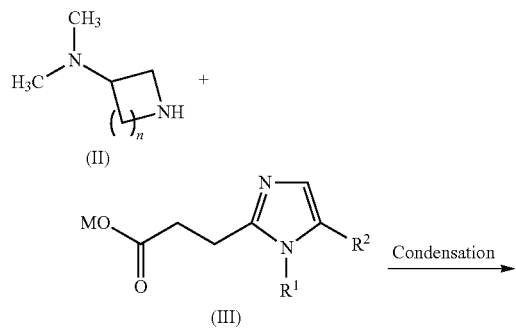

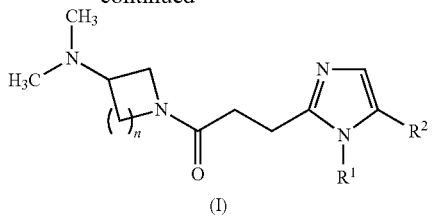

wherein M represents a hydrogen atom or an alkali metal such as lithium or sodium, and other reference symbols are the same as defined above.

A cyclic amine derivative represented by general formula (I) (hereinafter referred to as a cyclic amine derivative (I) and the derivatives represented by other general formulas are simply described in the same manner) can be obtained, for example, by the condensation reaction between a 3-dimethylaminocyclic amine derivative (II) and a carboxylic acid derivative (III) by use of a condensing agent in the presence or absence of a base.

In the condensation reaction, a 3-dimethylaminocyclic amine derivative (II) and a salt thereof can be used. As the salt herein, for example, the same salt as a pharmacologically acceptable salt as mentioned above can be mentioned.

As the 3-dimethylaminocyclic amine derivative (II) and carboxylic acid derivative (III) to be used in the condensation reaction, commercially available compounds can be directly used. However, they can be synthesized, for example, in accordance with the production methods that will be described below.

As the base to be used in the condensation reaction, for example, an aromatic amine such as pyridine or lutidine; or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mol of a 3-dimethylaminocyclic amine derivative (II) and more preferably 0.8 to 5.0 moles.

As the condensing agent to be used in the condensation reaction, for example, O-(benzotriazol-1-yl)-N,N,N',N'-tetramethyluronium hexafluorophosphate (HBTU), cyclohexylcar-bodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphorylazide (DPPA), 4-(4,6-dimethoxy-1,3,5-triazin-2-yl)-4-methylmorpholinium chloride (DMTMM), isobutyl chloroformate, diethylacetyl chloride or trimethylacetyl chloride can be mentioned. These condensing agents are used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a 3-dimethylaminocyclic amine derivative (II) and more preferably 0.8 to 5.0 moles.

The amount of the carboxylic acid derivative (III) to be used in the condensation reaction is preferably 0.5 to 3 moles relative to 1 mole of a 3-dimethylaminocyclic amine derivative (II) and more preferably 0.8 to 1.5 moles.

The condensation reaction is generally performed in a solvent. The solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; an amide such as N,N-dimethylformamide or N-methylpyrrolidone; an alcohol such as methanol, ethanol or 2-propanol; or an aliphatic nitrile such as acetonitrile or propionitrile can be mentioned. A mixed solvent of these may be used. When an aromatic amine such as pyridine is selected as the solvent, a condensation reaction can be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 48 hours.

2. Salt Formation Steps of Cyclic Amine Derivative (I):

Pharmacologically acceptable salts of a cyclic amine derivative (I) can be obtained, for example, through a salt formation reaction performed by mixing the cyclic amine derivative (I) and an acid.

As the acid to be used for a salt formation reaction, for example, an inorganic acid such as hydrochloric acid, sulfuric acid, phosphoric acid or hydrobromic acid; and an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoic acid, pamoic acid, ascorbic acid, adipic acid, methanesulfonic acid, p-toluene-sulfonic acid or cinnamic acid can be mentioned.

A salt formation reaction is generally performed in a solvent. The solvent that does not inhibit the reaction is appropriately selected. As the solvent, for example, an aliphatic alcohol such as methanol, ethanol or isopropanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate; or water can be mentioned. A mixture of these solvents may be used.

3. Production Method for 3-Dimethylaminocyclic Amine Derivative (II):

wherein PG represents a protective group and n is the same as defined above.

Step 1

A 3-dimethylaminocyclic amine derivative (V) can be obtained by the reductive amination reaction between a ketocyclic amine derivative (IV) and a dimethylamine.

As the ketocyclic amine derivative (IV) to be used as the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 2

A 3-dimethylaminocyclic amine derivative (V) can be obtained by the reductive alkylation reaction between a 3-aminocyclic amine derivative (VI) and formaldehyde.

As the 3-aminocyclic amine derivative (VI) to be used in the reductive alkylation reaction, a commercially available compound can be directly used.

The reductive alkylation reaction can be performed in accordance with a known method (for example, Journal of Organic Chemistry, vol. 68, p. 770-779, 2003) or a similar method thereto.

Step 3

A 3-dimethylaminocyclic amine derivative (II) can be obtained by deprotection of a 3-dimethylaminocyclic amine derivative (V).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

4. Production Method for Carboxylic Acid Derivative (III):

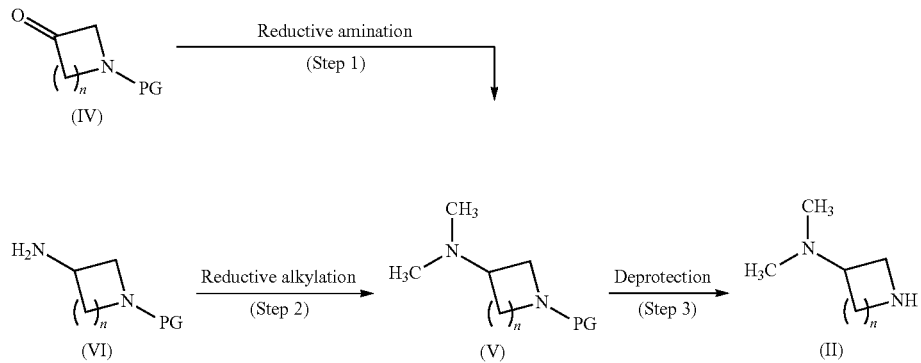

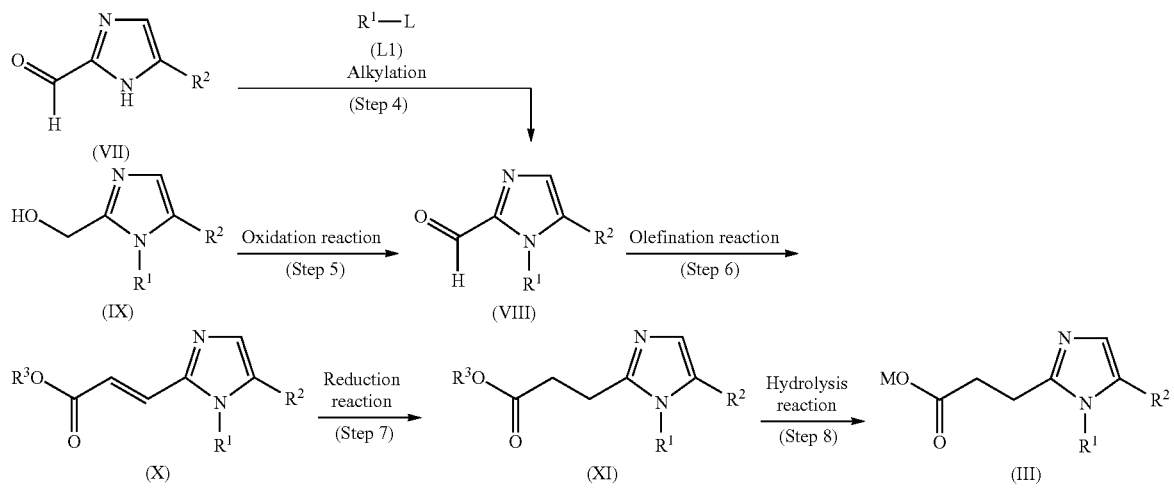

wherein L represents a leaving group such as a chlorine atom, a bromine atom or an iodine atom, $R^3$ represents an alkyl group having 1 to 6 carbon atoms such as a methyl group, an ethyl group, a n-propyl group or a n-butyl group, and other individual reference symbols are the same as defined above.

Step 4

A 2-formylimidazole derivative (VIII) can be obtained by removing a proton from a 2-formylimidazole derivative (VII) with a base and then applying an alkylating reagent (LI) to carry out the alkylation reaction.

As the 2-formylimidazole derivative (VII) to be used in the alkylation reaction, a commercially available compound can be directly used.

As the base to be used in the alkylation reaction, for example, a metal carbonate such as sodium carbonate, potassium carbonate or cesium carbonate; or an alkali metal hydroxide such as sodium hydroxide or potassium hydroxide can be mentioned.

The amount of the base to be used in the alkylation reaction is preferably 0.5 to 3.0 moles relative to 1 mole of a 2-formylimidazole derivative (VII) and more preferably 0.8 to 2.0 moles.

The amount of the alkylating reagent (LI) to be used in the alkylation reaction is preferably 0.5 to 3.0 moles relative to 1 mole of a 2-formylimidazole derivative (VII) and more preferably 0.8 to 2.0 moles.

The alkylation reaction is generally performed in a solvent. The solvent that does not inhibit the reaction is appropriately selected. As the solvent, for example, an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 5

A 2-formylimidazole derivative (VIII) can be obtained by the oxidation reaction of an alcohol derivative (IX).

As the alcohol derivative (IX) to be used in the oxidation reaction, a commercially available compound can be directly used. However, the alcohol derivative (IX) can be synthesized by a known method.

As the oxidant to be used in the oxidation reaction, for example, sulfur trioxide-pyridine, activated dimethyl sulfoxide or a Dess-Martin reagent can be mentioned.

The amount of the oxidant to be used in the oxidation reaction is preferably 0.5 to 3.0 moles relative to 1 mole of an alcohol derivative (IX) and more preferably 0.8 to 2.0 moles.

The oxidation reaction is generally performed in a solvent. The solvent that does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixture of these solvents may be used.

In the oxidation reaction, the reaction temperature is preferably −78° C. to 100° C. and more preferably −78° C. to 40° C.

In the oxidation reaction, the reaction time, which varies depending upon the reaction conditions, is preferably 5 minutes to 72 hours, and more preferably 30 minutes to 48 hours.

Step 6

An acrylic acid ester derivative (X) can be obtained by the olefination reaction of a 2-formylimidazole derivative (VIII).

As the reagent to be used in the olefination reaction, for example, a Wittig reagent such as methyl 2-(triphenylphosphoranylidene)acetate; or a Horner-Emmons reagent such as ethyl diethylphosphonoacetate can be mentioned. As the Wittig reagent or Horner-Emmons reagent, a commercially available compound can be directly used.

The amount of the Wittig reagent or Horner-Emmons reagent to be used in the olefination reaction is preferably 0.5 to 3.0 moles relative to 1 mole of a 2-formylimidazole derivative (VIII) and more preferably 0.8 to 2.0 moles.

The olefination reaction is generally performed in a solvent. The solvent that does not inhibit the reaction is appropriately selected. As the solvent, for example, an aromatic hydrocarbon such as toluene, chlorobenzene or xylene; an ether such as tetrahydrofuran or 1,4-dioxane; an amide such as N,N-dimethylformamide or N-methylpyrrolidone; or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 7

An ester derivative (XI) can be obtained by the reduction reaction of an acrylic acid ester derivative (X) in the presence of a transition metal catalyst under a hydrogen atmosphere.

As the transition metal catalyst to be used in the reduction reaction, for example, palladium-carbon can be mentioned.

The amount of the transition metal catalyst to be used in the reduction reaction is preferably 0.1 to 100 wt % relative to an acrylic acid ester derivative (X) and more preferably 1 to 50 wt %.

The reduction reaction is generally performed in a solvent. The solvent that does not inhibit the reaction is appropriately selected. As the solvent, for example, an aliphatic hydrocarbon such as heptane or hexane; or an aliphatic alcohol such as methanol, ethanol or propanol can be mentioned. A mixture of these solvents may be used.

In the reduction reaction, the reaction temperature is preferably 0 to 80° C. and more preferably 10 to 40° C.

In the reduction reaction, the reaction time, which varies depending upon the reaction conditions, is preferably 5 minutes to 72 hours, and more preferably 30 minutes to 48 hours.

Step 8

A carboxylic acid derivative (III) can be obtained by the hydrolysis reaction of an ester derivative (XI).

As the base to be used in the hydrolysis reaction, for example, lithium hydroxide, potassium hydroxide or sodium hydroxide can be mentioned.

The amount of the base to be used in the hydrolysis reaction is preferably 0.5 to 3.0 moles relative to 1 mole of an ester derivative (XI) and more preferably 0.8 to 2.0 moles.

The hydrolysis reaction is generally performed in a solvent and a solvent that does not inhibit the reaction is appropriately selected. As the solvent, for example, an aliphatic alcohol such as methanol, ethanol or propanol; or water can be mentioned. A mixture of these solvents may be used.

In the hydrolysis reaction, the reaction temperature is preferably, −20° C. to 150° C. and more preferably 0 to 100° C.

In the hydrolysis reaction, the reaction time, which varies depending upon the reaction conditions, is preferably 5 minutes to 72 hours, and more preferably 30 minutes to 48 hours.

The analgesic action of a cyclic amine derivative (I) or a pharmacologically acceptable salt thereof, particularly the therapeutic effect on neuropathic pain can be evaluated by use of an appropriate animal model. As the appropriate animal model for neuropathic pain, for example, a mouse or rat partial sciatic nerve ligation model (Malmberg et al., Pain, vol. 76, p. 215-222, 1998) or a mouse or rat spinal nerve ligation model (Kim et al., Pain, vol. 50, p. 355-363, 1992) can be mentioned.

The cyclic amine derivative (I) or a pharmacologically acceptable salt thereof, since it has an excellent analgesic action, particularly a therapeutic effect on neuropathic pain, can be used as a medicine, preferably used as an analgesic agent, and particularly preferably as a therapeutic agent for neuropathic pain.

A cyclic amine derivative (I) or a pharmacologically acceptable salt thereof can be used as an analgesic agent, particularly a therapeutic agent for neuropathic pain, available for long term administration because central nervous system adverse effects are reduced.

As the neuropathic pain herein, for example, cancer pain, shingles pain, postherpetic neuralgia, AIDS-related neuralgia, painful diabetic neuropathy or trigeminal neuralgia can be mentioned.

The cyclic amine derivative (I) or a pharmacologically acceptable salt thereof is also useful for treating acute and chronic pain. The acute pain usually lasts for a short period and, for example, postoperative pain, pain after tooth extraction or trigeminal neuralgia can be mentioned. The chronic pain is defined as pain usually lasting for 3 to 6 months and includes somatogenic pain and psychogenic pain and, for example, chronic rheumatoid arthritis, osteoarthritis or postherpetic neuralgia can be mentioned.

A medicine containing a cyclic amine derivative (I) or a pharmacologically acceptable salt as an active ingredient, exerts an excellent analgesic action, particularly a therapeutic effect on neuropathic pain when it is administered to a mammal (for example, mouse, rat, hamster, rabbit, cat, dog, cow, sheep, monkey or human), especially to a human.

When a cyclic amine derivative (I) or a pharmacologically acceptable salt thereof is used as a medicine, the cyclic amine derivative (I) or a pharmacologically acceptable salt thereof directly or in combination with a pharmaceutically acceptable carrier can be orally or parenterally administered.

As the dosage form when a medicine containing a cyclic amine derivative (I) or a pharmacologically acceptable salt thereof as an active ingredient is orally administered, for example, tablets (including sugar-coated and film-coated tablets), pills, granules, powders, capsules (including soft capsules and micro capsules), syrups, emulsions or suspensions can be mentioned. As the dosage form when a medicine containing a cyclic amine derivative (I) or a pharmacologically acceptable salt thereof as an active ingredient is parenterally administered, for example, injections, infusions, drops, suppositories, endermic liniments or adhesive patches can be mentioned. It is further effective to prepare a sustained-release formulation by using an appropriate base (for example, a butyric acid polymer, a glycolic acid polymer, a butyric acid-glycolic acid copolymer, mixtures of a butyric acid polymer and a glycolic acid polymer, or a polyglycerol fatty acid ester) in combination.

Formulations having the aforementioned dosage forms can be prepared in accordance with production methods known in the field of drug formulation. In this case, if necessary, production can be made by adding an excipient, a binder, a lubricant, a disintegrating agent, a sweetening agent, a surfactant, a suspending agent or an emulsifying agent, which is generally used in the field of drug formulation.

Tablets can be prepared, for example, by adding an excipient, a binder, a disintegrating agent or a lubricant. Pills and granules can be prepared by adding, for example, an excipient, a binder or a disintegrating agent. Powders and capsules can be prepared by adding, for example, an excipient. Syrups can be prepared by adding, for example, a sweetening agent. Emulsions or suspensions can be prepared by adding, for example, a surfactant, a suspending agent or an emulsifier.

As the excipient, for example, lactose, glucose, starch, sucrose, microcrystalline cellulose, powdered glycyrrhiza, mannitol, sodium hydrogen carbonate, calcium phosphate or calcium sulfate can be mentioned.

As the binder, for example, a starch paste solution, a gum arabic solution, a gelatin solution, a tragacanth solution, a carboxymethylcellulose solution, a sodium alginate solution or glycerin can be mentioned.

As the disintegrating agent, for example, starch or calcium carbonate can be mentioned.

As the lubricant, for example, magnesium stearate, stearic acid, calcium stearate or purified talc can be mentioned.

As the sweetening agent, for example, glucose, fructose, invert sugar, sorbitol, xylitol, glycerin or simple syrup can be mentioned.

As the surfactant, for example, sodium lauryl sulfate, polysorbate 80, sorbitan monofatty acid ester or stearic acid polyoxyl 40 can be mentioned.

As the suspending agent, for example, Gum arabic, sodium alginate, sodium carboxymethylcellulose, methyl cellulose or bentonite can be mentioned.

As the emulsifier, for example, Gum arabic, tragacanth, gelatin or polysorbate 80 can be mentioned.

When a medicine containing a cyclic amine derivative (I) or a pharmacologically acceptable salt thereof as an active ingredient is prepared in the aforementioned dosage forms, a coloring agent, a preserving agent, a fragrance, a flavoring agent, a stabilizer or a thickener generally used in the field of drug formulation can be added.

The dose per day of a medicine containing a cyclic amine derivative (I) or a pharmacologically acceptable salt thereof as an active ingredient varies depending upon e.g., the state or body weight of the patient or the type or administration route of a compound. For example, in the case of oral administration to an adult (weight: about 60 kg), the amount of the cyclic amine derivative (I) or a pharmacologically acceptable salt thereof serving as an active ingredient falls within the range of 1 to 1000 mg and administration is preferably made in 1 to 3 divided doses. In the case of parenteral administration to an adult (weight: about 60 kg) by an injectable solution, the amount of the cyclic amine derivative (I) or a pharmacologically acceptable salt thereof serving as an active ingredient in e.g., an injection, falls within the range of 0.01 to 100 mg per body weight (1 kg). The injectable solution is preferably intravenously administered.

A cyclic amine derivative (I) or a pharmacologically acceptable salt thereof may be used in combination with other medicinal agents in an appropriate blending ratio to supplement or enhance a therapeutic or prophylactic effect or reduce the dose. In this case, as the other medicinal agents, for example, an antidepressant such as amitriptyline, milnacipran or duloxetine; an anxiolytic such as alprazolam; an anticonvulsant such as carbamazepine; a local anesthetic such as lidocaine; a sympathetic agonist such as adrenaline; an NMDA receptor antagonist such as ketamine; a GABA transaminase inhibitor such as sodium valproate; a calcium channel blocker such as pregabalin; a serotonin receptor antagonist such as risperidone; a GABA receptor function enhancer such as diazepam; or an anti-inflammatory drug such as diclofenac can be mentioned.

EXAMPLES

Our derivatives, agents, medicines, methods and treatments will be described in detail below with reference to Examples and Reference Examples. However, this disclosure is not limited to them.

In the following description, the names of the solvents shown in the NMR data represent the solvents used in the measurement. The 400 MHz NMR spectra were measured by using JNM-AL 400 series Nuclear Magnetic Resonance (NMR) spectrometer (JEOL, Ltd.). Chemical shifts are expressed by δ (unit: ppm) using tetramethylsilane as the reference, and the respective signals, respectively have the following meanings: s (singlet), d (doublet), t (triplet), q (quartet), quint (quintet), sept (septet), m (multiplet), br (broad), dd (double doublet), dt (double triplet), ddd (double double doublet), dq (double quartet), td (triple doublet), and tt (triple triplet). The ESI-MS spectra were measured by using Agilent Technologies 1200 Series, G6130A (from Agilent Technology). Commercially available products were used for all the solvents. For flash chromatography, YFLC W-prep2XY (from YAMAZEN) was used.

Raw materials and intermediates of cyclic amine derivatives (I) were synthesized by the methods described in the following Reference Examples. Commercially-available products were used for the compounds used in synthesizing the compounds of Reference Examples for which synthesis methods are not described below.

Reference Example 1: Synthesis of N,N-dimethylazetidin-3-amine Hydrochloride

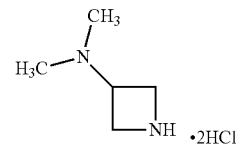

A solution of dimethylamine in tetrahydrofuran (2.0 M, 0.185 mL, 3.65 mmol), acetic acid (0.017 mL, 0.292 mmol) and sodium triacetoxyborohydride (0.232 g, 1.10 mmol) were added to a solution of tert-butyl 3-oxoazetidine-1-carboxylate (0.500 g, 2.92 mmol) in dichloromethane (12.0 mL) at 0° C. The reaction liquid was stirred at the same temperature for 30 minutes, and then sodium triacetoxyborohydride (0.232 g, 1.10 mmol) was added at 0° C. The reaction liquid was stirred at the same temperature for 30 minutes, and then sodium triacetoxyborohydride (0.464 g, 2.19 mmol) was added at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by column chromatography (silica gel, chloroform/methanol). 1,4-Dioxane (4.0 mL) was added to the resulting residue at room temperature to dissolve the residue. A solution of hydrogen chloride in 1,4-dioxane (4.0 N, 4.04 mL, 16.2 mmol) was added to the reaction liquid at room temperature and the reaction liquid was stirred at the same temperature for 3 hours. The white solid precipitated was filtered and collected, washed with hexane, dried at room temperature to obtain a crude product of N,N-dimethylazetidin-3-amine hydrochloride as a white solid.

Reference Example 2: Synthesis of (S)—N,N-dimethylpiperidin-3-amine Hydrochloride

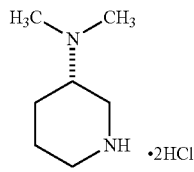

An aqueous solution of formaldehyde (35%, 0.884 mL, 11.2 mmol), acetic acid (0.029 mL, 0.50 mmol) and sodium triacetoxyborohydride (0.278 g, 1.31 mmol) were added to a solution of (S)-tert-butyl 3-aminopiperidine-1-carboxylate (0.500 g, 2.50 mmol) in dichloromethane (12.0 mL) at 0° C. After the reaction liquid was stirred at the same temperature for 30 minutes, sodium triacetoxyborohydride (0.278 g, 1.31 mmol) was added at 0° C. After the reaction liquid was stirred at the same temperature for 30 minutes, sodium triacetoxyborohydride (0.556 g, 2.62 mmol) was added at 0° C. The reaction liquid was stirred at room temperature for 60 hours and cooled to 0° C. A saturated aqueous solution of sodium hydrogencarbonate was added to the reaction liquid and the reaction liquid was extracted with chloroform. The organic layer was dried over anhydrous sodium sulfate and filtered and the filtrate was concentrated under reduced pressure. The residue was purified by column chromatography (NH silica gel, chloroform/methanol). Diethyl ether (15.0 mL) was added to the resulting residue at room temperature to dissolve the residue. A solution of hydrogen chloride in diethyl ether (2.0 N, 7.49 mL, 15.0 mmol) was added to the reaction liquid at 0° C. and the reaction liquid was stirred at room temperature for 3 hours. The white solid precipitated was filtered and collected, washed with diethyl ether and dried at room temperature to obtain a crude product of (S)—N,N-dimethylpiperidin-3-amine hydrochloride.

Reference Example 3: Synthesis of (R)—N,N-dimethylpiperidin-3-amine

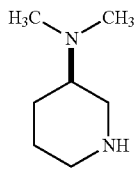

An aqueous solution of formaldehyde (37%, 2.55 g, 31.5 mmol), acetic acid (0.086 mL, 1.50 mmol) and sodium triacetoxyborohydride (4.00 g, 18.9 mmol) were added to a solution of (R)-tert-butyl 3-aminopiperidine-1-carboxylate (3.00 g, 15.0 mmol) in dichloromethane (30.0 mL) at 0° C. After the reaction liquid was stirred at the same temperature for 30 minutes, sodium triacetoxyborohydride (3.94 g, 18.6 mmol) was added at 0° C. The reaction liquid was stirred at room temperature for 28 hours and cooled to 0° C. A saturated aqueous solution of sodium hydrogencarbonate was added to the reaction liquid and the reaction liquid was extracted with dichloromethane. The organic layer was dried over anhydrous sodium sulfate and filtered and the filtrate was concentrated under reduced pressure. The residue was purified by column chromatography (NH silica gel, chloroform/methanol). Dichloromethane (60.0 mL) was added to the resulting residue at room temperature to dissolve the residue. Trifluoroacetic acid (11.5 mL, 150 mmol) was added to the reaction liquid at 0° C. The reaction liquid was stirred at room temperature for 3 hours and concentrated under reduced pressure. A 1N aqueous solution of sodium hydroxide was added to the resulting residue and the reaction liquid was extracted with dichloromethane. The organic layer was dried over anhydrous sodium sulfate and filtered. The filtrate was concentrated under reduced pressure to obtain a crude product of (R)—N,N-dimethylpiperidin-3-amine.

Reference Example 4: Synthesis of 1-isopropyl-1H-imidazole-2-carbaldehyde

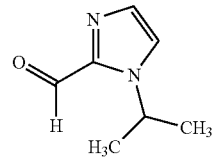

Potassium carbonate (0.863 g, 6.24 mmol) and 2-iodopropane (0.614 mL, 6.24 mmol) were added to a solution of 1H-imidazole-2-carbaldehyde (0.500 g, 5.20 mmol) in N,N-dimethyl formamide (5.2 mL) at room temperature. The reaction liquid was stirred at 60° C. for 4 hours. The reaction liquid was cooled to room temperature. Ethyl acetate and distilled water were added to the reaction liquid and the reaction liquid was extracted with ethyl acetate. The organic layer was washed with a 10% aqueous solution of sodium chloride, dried over anhydrous sodium sulfate and filtered. The filtrate was concentrated under reduced pressure. The residue was purified by column chromatography (silica gel, n-hexane/ethyl acetate) to obtain 1-isopropyl-1H-imidazole-2-carbaldehyde (0.355 g, 2.57 mmol, 49%) as a colorless oil.

$^1$H-NMR (400 MHz, CDCl$_3$) δ: 1.48 (3H, d, J=6.4 Hz), 1.48 (3H, d, J=6.4 Hz), 5.48 (1H, quint, J=6.4 Hz), 7.30 (1H, s), 7.33 (1H, s), 9.83 (1H, s).

ESI-MS: m/z=139 (M+H)$^+$.

Reference Example 5: Synthesis of 1-(2-methoxyethyl)-1H-imidazole-2-carbaldehyde

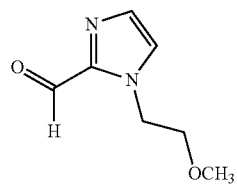

Potassium carbonate (1.44 g, 10.4 mmol) and 1-bromo-2-methoxyethane (0.545 mL, 5.72 mmol) were added to a solution of 1H-imidazole-2-carbaldehyde (0.500 g, 5.20 mmol) in N,N-dimethyl formamide (5.2 mL) at room temperature. The reaction liquid was stirred at 60° C. for 5 hours. The reaction liquid was cooled to room temperature. Ethyl acetate and distilled water were added to the reaction liquid and the reaction liquid was extracted with ethyl acetate. The organic layer was washed with a 10% aqueous solution of sodium chloride, dried over anhydrous sodium sulfate and filtered. The filtrate was concentrated under reduced pressure. The residue was purified by column chromatography (silica gel, n-hexane/ethyl acetate) to obtain 1-(2-methoxyethyl)-1H-imidazole-2-carbaldehyde (0.113 g, 0.733 mmol, 14%) as a white solid.

$^1$H-NMR (400 MHz, DMSO) δ: 3.21 (3H, s), 3.61 (2H, d, J=5.2 Hz), 4.53 (2H, d, J=5.2 Hz), 7.27 (1H, s), 7.62 (1H, s), 9.69 (1H, s).

ESI-MS: m/z=155 (M+H)$^+$.

Reference Example 6: Synthesis of 1-(2,2,2-trifluoroethyl)-1H-imidazole-2-carbaldehyde

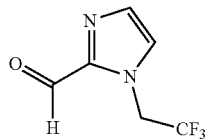 [SMILES: O=Cc1nccn1CC(F)(F)F]

A Dess-Martin reagent (1.02 g, 2.40 mmol) was added to a solution of (1-(2,2,2-trifluoroethyl)-1H-imidazol-2-yl)methanol (0.360 g, 2.00 mmol) in dichloromethane (20.0 mL) at 0° C. The reaction liquid was stirred at room temperature for 1 hour. The reaction liquid was filtered through Celite and the filtrate was concentrated under reduced pressure. The residue was purified by column chromatography (silica gel, n-hexane/ethyl acetate) to obtain 1-(2,2,2-trifluoroethyl)-1H-imidazole-2-carbaldehyde (0.313 g, 1.76 mmol, 88%) as a white solid.

$^1$H-NMR (400 MHz, CDCl$_3$) δ: 5.16 (2H, q, J=8.0 Hz), 7.25 (1H, brs), 7.38 (1H, brs), 9.83-9.85 (1H, m).

ESI-MS: m/z=179 (M+H)$^+$.

Reference Example 7: Synthesis of 5-chloro-1-methyl-1H-imidazole-2-carbaldehyde

A Dess-Martin reagent (1.04 g, 2.46 mmol) was added to a solution of (5-chloro-1-methyl-1H-imidazol-2-yl)methanol (0.300 g, 2.05 mmol) in dichloromethane (20.0 mL) at 0° C. The reaction liquid was stirred at room temperature for 4 hours. The reaction liquid was filtered through Celite and the filtrate was concentrated under reduced pressure. The residue was purified by column chromatography (silica gel, n-hexane/ethyl acetate) to obtain 5-chloro-1-methyl-1H-imidazole-2-carbaldehyde (0.289 g, 2.00 mmol, 98%) as a white solid.

$^1$H-NMR (400 MHz, CDCl$_3$) δ: 3.97 (3H, s), 7.24 (1H, s), 9.70 (1H, s).

ESI-MS: m/z=145 (M+H)$^+$.

Reference Example 8: Synthesis of (E)-methyl 3-(1-methyl-1H-imidazol-2-yl)acrylate

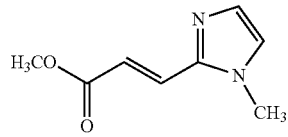

Methyl (triphenylphosphoranylidene)acetate (33.4 g, 99.9 mmol) was added to a solution of 1-methyl-1H-imidazole-2-carbaldehyde (10.0 g, 90.8 mmol) in dichloromethane (240 mL) at room temperature. The reaction liquid was stirred for 16 hours and then concentrated under reduced pressure. The residue was washed with a mixed solvent of n-hexane/dichloromethane=19/1 and the washing solution was concentrated. The residue was purified by column chromatography (silica gel, n-hexane/ethyl acetate) to obtain (E)-methyl 3-(1-methyl-1H-imidazol-2-yl)acrylate (11.9 g, 71.6 mmol, 79%) as a white solid.

$^1$H-NMR (400 MHz, CDCl$_3$) δ: 3.76 (3H, s), 3.81 (3H, s), 6.82 (1H, d, J=15.6 Hz), 6.98 (1H, brs), 7.16 (1H, brs), 7.53 (1H, d, J=15.6 Hz).

ESI-MS: m/z=167 (M+H)$^+$.

Reference Example 9: Synthesis of (E)-methyl 3-(1-isopropyl-1H-imidazol-2-yl)acrylate

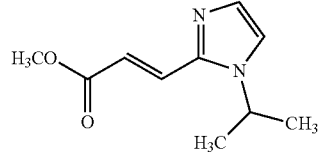

Methyl (triphenylphosphoranylidene)acetate (0.932 g, 2.79 mmol) was added to a solution of 1-isopropyl-1H-imidazole-2-carbaldehyde (0.350 g, 2.53 mmol) in dichloromethane (7.6 mL) at room temperature. The reaction liquid was stirred for 16 hours and then concentrated under reduced pressure. The residue was washed with a mixed solvent of n-hexane/dichloromethane=20/1 and the washing solution was concentrated. The residue was purified by column chromatography (silica gel, n-hexane/ethyl acetate) to obtain (E)-methyl 3-(1-isopropyl-1H-imidazol-2-yl)acrylate (0.362 g, 1.86 mmol, 74%) as a white solid.

$^1$H-NMR (400 MHz, CDCl$_3$) δ: 1.50 (3H, d, J=6.4 Hz), 1.50 (3H, d, J=6.4 Hz), 3.81 (3H, s), 4.62 (1H, quint, J=6.4 Hz), 6.87 (1H, d, J=15.6 Hz), 7.10 (1H, brs), 7.18 (1H, brs), 7.56 (1H, d, J=15.6 Hz).

ESI-MS: m/z=195 (M+H)$^+$.

Reference Example 10: Synthesis of (E)-methyl 3-(1-(2,2,2-trifluoroethyl)-1H-imidazol-2-yl)acrylate

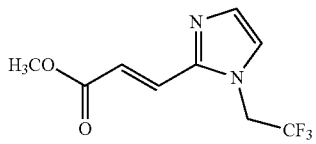 [SMILES: COC(=O)/C=C/c1nccn1CC(F)(F)F]

Methyl (triphenylphosphoranylidene)acetate (0.640 g, 1.92 mmol) was added to a solution of 1-(2,2,2-trifluoroethyl)-1H-imidazole-2-carbaldehyde (0.313 g, 1.76 mmol) in dichloromethane (5.0 mL) at room temperature. The reaction liquid was stirred for 16 hours and then concentrated under reduced pressure. The residue was washed with a mixed solvent of n-hexane/dichloromethane=20/1 and the washing solution was concentrated. The residue was purified by column chromatography (silica gel, n-hexane/ethyl acetate) to obtain (E)-methyl 3-(1-(2,2,2-trifluoroethyl)-1H-imidazol-2-yl)acrylate (0.320 g, 1.37 mmol, 78%) as a white solid.

$^1$H-NMR (400 MHz, CDCl$_3$) δ: 3.82 (3H, s), 4.56-4.64 (2H, m), 6.93 (1H, d, J=15.2 Hz), 7.10 (1H, brs), 7.24 (1H, brs), 7.44 (1H, d, J=15.2 Hz).

ESI-MS: m/z=235 (M+H)$^+$.

Reference Example 11: Synthesis of (E)-ethyl 3-(1-(2-methoxyethyl)-1H-imidazol-2-yl)acrylate

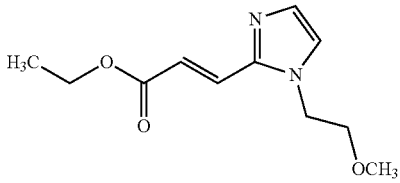 [SMILES: CCOC(=O)/C=C/c1nccn1CCOC]

Ethyl diethylphosphonoacetate (1.99 mL, 9.92 mmol) was added to a suspension solution of sodium hydride (0.455 g, 10.4 mmol, 55%) in tetrahydrofuran (49.6 mL) under ice cooling. After the reaction liquid was stirred at the same temperature for 60 minutes, a solution of 1-(2-methoxyethyl)-1H-imidazole-2-carbaldehyde (1.53 g, 9.92 mmol) in tetrahydrofuran (10 mL) was added. The reaction liquid was stirred at room temperature for 3 hours. A saturated aqueous solution of ammonium chloride was added to the reaction liquid and the reaction liquid was extracted with ethyl acetate. The organic layer was washed with a 10% aqueous solution of sodium chloride, dried over anhydrous sodium sulfate and filtered. The filtrate was concentrated under reduced pressure. The residue was purified by column chromatography (silica gel, n-hexane/ethyl acetate) to obtain (E)-ethyl-3-(1-(2-methoxyethyl)-1H-imidazol-2-yl)acrylate (1.80 g, 8.03 mmol, 81%) as a colorless oil.

$^1$H-NMR (400 MHz, CDCl$_3$) δ: 1.32 (3H, t, J=7.2 Hz), 3.32 (3H, s), 3.63 (2H, t, J=5.2 Hz), 4.20 (2H, t, J=5.2 Hz), 4.26 (2H, q, J=7.2 Hz), 6.84 (1H, d, J=15.4 Hz), 7.08 (1H, brs), 7.16 (1H, brs), 7.52 (1H, d, J=15.4 Hz).

ESI-MS: m/z=225 (M+H)$^+$.

Reference Example 12: Synthesis of (E)-methyl 3-(5-chloro-1-methyl-1H-imidazol-2-yl)acrylate

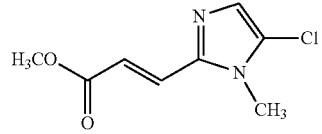

Methyl (triphenylphosphoranylidene)acetate (0.738 g, 2.21 mmol) was added to a solution of 5-chloro-1-methyl-1H-imidazole-2-carbaldehyde (0.289 g, 2.00 mmol) in dichloromethane (6.0 mL) at room temperature. The reaction liquid was stirred for 16 hours and then concentrated under reduced pressure. The residue was washed with a mixed solvent of n-hexane/dichloromethane=20/1 and the washing solution was concentrated. The residue was purified by column chromatography (silica gel, n-hexane/ethyl acetate) to obtain (E)-methyl 3-(5-chloro-1-methyl-1H-imidazol-2-yl)acrylate (0.312 g, 1.56 mmol, 78%) as a white solid.

$^1$H-NMR (400 MHz, CDCl$_3$) δ: 3.67-3.69 (3H, m), 3.80-3.82 (3H, m), 6.78-6.85 (1H, m), 7.08-7.10 (1H, m), 7.44-7.50 (1H, m).

ESI-MS: m/z=201 (M+H)$^+$.

Reference Example 13: Synthesis of 3-(1-methyl-1H-imidazol-2-yl)propanoic Acid

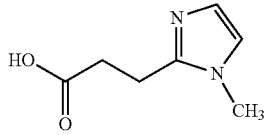

Palladium-carbon (10% wet, 15 mg) was added to a solution of (E)-methyl 3-(1-methyl-1H-imidazol-2-yl)acrylate (0.180 g, 1.08 mmol) in ethanol (4.0 mL) at room temperature. The reaction liquid was stirred under a hydrogen atmosphere for 4 hours. The reaction liquid was filtered through Celite and the filtrate was concentrated under reduced pressure. Methanol (1.0 mL) was added to the resulting residue at room temperature to dissolve the residue and the reaction liquid was cooled to 0° C. An aqueous solution of sodium hydroxide (1.0 N, 1.19 mL, 1.19 mmol) was added to the reaction liquid at 0° C. The reaction liquid was stirred at room temperature for 2 hours and concentrated under reduced pressure to obtain a crude product of 3-(1-methyl-1H-imidazol-2-yl)propanoic acid.

Reference Example 14: Synthesis of 3-(1-isopropyl-1H-imidazol-2-yl)propanoic Acid

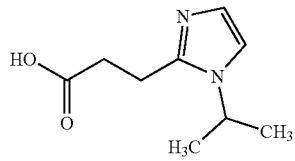

Palladium-carbon (10% wet, 65 mg) was added to a solution of (E)-methyl 3-1-isopropyl-1H-imidazol-2-yl) acrylate (0.670 g, 3.71 mmol) in methanol (14.8 mL) at room temperature. The reaction liquid was stirred under a hydrogen atmosphere for 16 hours. The reaction liquid was filtered through Celite and the filtrate was concentrated under reduced pressure. Methanol (3.7 mL) was added to the resulting residue at room temperature to dissolve the residue and the reaction liquid was cooled to 0° C. An aqueous solution of sodium hydroxide (1.0 N, 4.07 mL, 4.07 mmol) was added to the reaction liquid at 0° C. and the reaction liquid was stirred at room temperature for 16 hours, concentrated under reduced pressure to obtain a crude product of 3-(1-isopropyl-1H-imidazol-2-yl)propanoic acid.

Reference Example 15: Synthesis of 3-(1-(2,2,2-trifluoroethyl)-1H-imidazol-2-yl)propanoic Acid

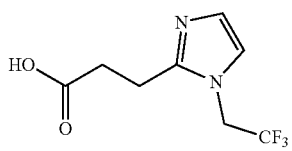

Palladium-carbon (10% wet, 36 mg) was added to a solution of (E)-methyl 3-(1-(2,2,2-trifluoroethyl)-1H-imidazol-2-yl)acrylate (0.160 g, 0.683 mmol) in ethanol (7.0 mL) at room temperature. The reaction liquid was stirred under a hydrogen atmosphere for 16 hours and filtered through Celite. The filtrate was concentrated under reduced pressure. Methanol (2.0 mL) was added to the resulting residue at room temperature to dissolve the residue. The reaction liquid was cooled to 0° C. An aqueous solution of sodium hydroxide (1.0 N, 2.05 mL, 2.05 mmol) was added to the reaction liquid at 0° C. and the reaction liquid was stirred at room temperature for 4 hours. After a 1.0 N aqueous solution of hydrogen chloride was added to the reaction liquid to neutralize, the reaction liquid was concentrated under reduced pressure to obtain a crude product of 3-(1-(2,2,2-trifluoroethyl)-1H-imidazol-2-yl)propanoic acid.

Reference Example 16: Synthesis of 3-(1-(2-methoxyethyl)-1H-imidazol-2-yl)propanoic Acid

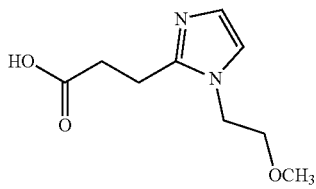

Palladium-carbon (10% wet, 0.180 g) was added to a solution of (E)-ethyl 3-(1-(2-methoxyethyl)-1H-imidazol-2-yl)acrylate (1.80 g, 8.03 mmol) in methanol (32.0 mL) at room temperature. The reaction liquid was stirred under a hydrogen atmosphere for 15 hours. The reaction liquid was filtered through Celite and the filtrate was concentrated under reduced pressure. Methanol (8.0 mL) was added to the resulting residue at room temperature to dissolve the residue. The reaction liquid was cooled to 0° C. An aqueous solution of sodium hydroxide (1.0 N, 8.43 mL, 8.43 mmol) was added to the reaction liquid at the same temperature. The temperature of the reaction liquid was raised to room temperature and the reaction liquid was stirred for 3 hours. After a 1.0 N aqueous solution of hydrogen chloride was added to the reaction liquid to neutralize, the reaction liquid was concentrated under reduced pressure. Ethanol was added to the residue and a precipitate was filtered. The filtrate was concentrated under reduced pressure to obtain a crude product of 3-(1-(2-methoxyethyl)-1H-imidazol-2-yl)propanoic acid.

Reference Example 17: Synthesis of methyl 3-(5-chloro-1-methyl-1H-imidazol-2-yl)propanoate

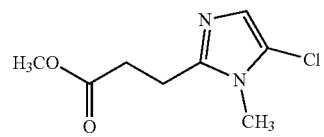

Platinum oxide (IV valence, 0.027 g, 0.120 mmol) was added to a solution of (E)-methyl 3-(5-chloro-1-methyl-1H-imidazol-2-yl)acrylate (0.240 g, 1.20 mmol) in ethanol (12.0 mL) at room temperature. The reaction liquid was stirred under a hydrogen atmosphere for 6 hours. The reaction liquid was filtered through Celite and the filtrate was concentrated under reduced pressure. The residue was purified by column chromatography (silica gel, n-hexane/ethyl acetate) to obtain methyl 3-(5-chloro-1-methyl-1H-imidazol-2-yl)propanoate (0.104 g, 0.513 mmol, 43%) as a white solid.

$^1$H-NMR (400 MHz, CDCl$_3$) δ: 2.84-2.96 (4H, m), 3.53 (3H, s), 3.70 (3H, s), 6.84 (1H, s).

ESI-MS: m/z=203 (M+H)$^+$.

Reference Example 18: Synthesis of 3-(5-chloro-1-methyl-1H-imidazol-2-yl)propanoic Acid

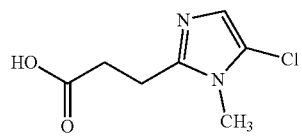

An aqueous solution of sodium hydroxide (1.0 N, 0.543 mL, 0.543 mmol) was added to a solution of methyl 3-(5-chloro-1-methyl-1H-imidazol-2-yl)propanoate (0.100 g, 0.493 mmol) in methanol (1.0 mL) at 0° C. The reaction liquid was stirred at room temperature for 4 hours. After a 1.0 N aqueous solution of hydrogen chloride was added to the reaction liquid to neutralize, the reaction liquid was concentrated under reduced pressure to obtain a crude product of 3-(5-chloro-1-methyl-1H-imidazol-2-yl)propanoic acid.

Example 1: Synthesis of 1-(3-(dimethylamino)azetidin-1-yl)-3-(1-methyl-1H-imidazol-2-yl)propan-1-one

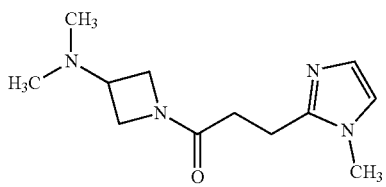 [SMILES: CN(C)C1CN(C(=O)CCc2nccn2C)C1]

Diisopropylethylamine (0.204 mL, 1.17 mmol), HBTU (0.177 g, 0.467 mmol) and 3-(dimethylamino)azetidine hydrochloride (0.0674 g, 0.389 mmol) were added to a solution of 3-(1-methyl-1H-imidazol-2-yl)propanoic acid (0.0600 g, 0.389 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain 1-(3-(dimethylamino)azetidin-1-yl)-3-(1-methyl-1H-imidazol-2-yl)propan-1-one (0.0710 g, 0.300 mmol, 77%)(hereinafter referred to as the compound of Example 1) as a colorless oil.

$^1$H-NMR (400 MHz, CDCl$_3$) δ: 2.16 (6H, s), 2.62-2.68 (2H, m), 2.92-2.98 (2H, m), 3.02-3.09 (1H, m), 3.60 (3H, m), 3.78-3.85 (1H, m), 3.93-4.02 (2H, m), 4.11-4.17 (1H, m), 6.78 (1H, d, J=1.2 Hz), 6.91 (1H, d, J=1.2 Hz).

ESI-MS: m/z=237 (M+H)$^+$.

Example 2: Synthesis of (S)-1-(3-(dimethylamino)piperidin-1-yl)-3-(1-methyl-1H-imidazol-2-yl)propan-1-one

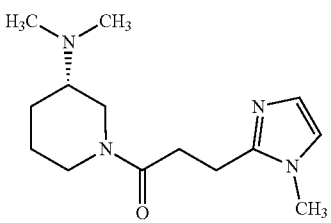

Diisopropylethylamine (0.204 mL, 1.17 mmol), HBTU (0.177 g, 0.467 mmol) and (S)-3-(dimethylamino)piperidine hydrochloride (0.0780 g, 0.389 mmol) were added to a solution of 3-(1-methyl-1H-imidazol-2-yl)propanoic acid (0.0600 g, 0.389 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain (S)-1-(3-(dimethylamino)piperidin-1-yl)-3-(1-methyl-1H-imidazol-2-yl)propan-1-one (0.0860 g, 0.325 mmol, 84%)(hereinafter referred to as the compound of Example 2) as a colorless oil.

$^1$H-NMR (400 MHz, CDCl$_3$) δ: 1.34-1.44 (2H, m), 1.92-2.24 (3H, m), 2.30 (6H, s), 2.40-2.57 (1H, m), 2.78-2.98 (5H, m), 3.60 (3H, s), 3.79-4.05 (1H, m), 4.44-4.67 (1H, m), 6.75-6.78 (1H, m), 6.88-6.90 (1H, m).

ESI-MS: m/z=265 (M+H)$^+$.

Example 3: Synthesis of (R)-1-(3-(dimethylamino)piperidin-1-yl)-3-(1-methyl-1H-imidazol-2-yl)propan-1-one

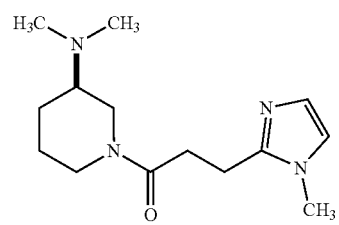

(R)-3-(dimethylamino)piperidine (0.0540 g, 0.425 mmol) and DMTMM (0.176 g, 0.638 mmol) were added to a solution of 3-(1-methyl-1H-imidazol-2-yl)propanoic acid (0.0980 g, 0.638 mmol) in methanol (4.3 mL) at room temperature. The reaction liquid was stirred at the same temperature for 3 hours. A saturated aqueous solution of potassium carbonate was added to the reaction liquid and the reaction liquid was extracted with chloroform. The organic layer was dried over anhydrous sodium sulfate and filtered. The filtrate was concentrated under reduced pressure. The residue was purified by column chromatography (NH silica gel, ethyl acetate/methanol) to obtain (R)-1-(3-(dimethylamino)piperidin-1-yl)-3-(1-methyl-1H-imidazol-2-yl)propan-1-one (0.0594 g, 0.225 mmol, 53%)(hereinafter referred to as the compound of Example 3) as a colorless oil.

$^1$H-NMR (400 MHz, CDCl$_3$) δ: 1.34-1.44 (2H, m), 1.92-2.24 (3H, m), 2.30 (6H, s), 2.40-2.57 (1H, m), 2.78-2.98 (5H, m), 3.60 (3H, s), 3.79-4.05 (1H, m), 4.44-4.67 (1H, m), 6.75-6.78 (1H, m), 6.88-6.90 (1H, m).

ESI-MS: m/z=265 (M+H)$^+$.

Example 4: Synthesis of 1-(3-(dimethylamino)azetidin-1-yl)-3-(1-isopropyl-1H-imidazol-2-yl)propan-1-one

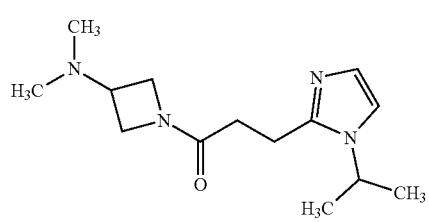 [SMILES: CC(C)n1ccnc1CCC(=O)N1CC(N(C)C)C1]

Diisopropylethylamine (0.201 mL, 1.15 mmol), HBTU (0.175 g, 0.461 mmol) and 3-(dimethylamino)azetidine hydrochloride (0.0665 g, 0.384 mmol) were added to a solution of 3-(1-isopropyl-1H-imidazol-2-yl)propanoic acid (0.0700 g, 0.384 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain 1-(3-(dimethylamino)azetidin-1-yl)-3-(1-isopropyl-1H-imidazol-2-yl)propan-1-one (0.0820 g, 0.310 mmol, 81%)(hereinafter referred to as the compound of Example 4) as a colorless oil.

$^1$H-NMR (400 MHz, CDCl$_3$) δ: 1.38-1.42 (6H, m), 2.16 (6H, s), 2.67-2.72 (2H, m), 2.93-3.09 (3H, m), 3.79-3.85 (1H, m), 3.95-4.02 (2H, m), 4.12-4.18 (1H, m), 4.39-4.47 (1H, m), 6.89-6.91 (1H, m), 6.94-6.95 (1H, m).

ESI-MS: m/z=265 (M+H)$^+$.

Example 5: Synthesis of (S)-1-(3-(dimethylamino)piperidin-1-yl)-3-(1-isopropyl-1H-imidazol-2-yl)propan-1-one

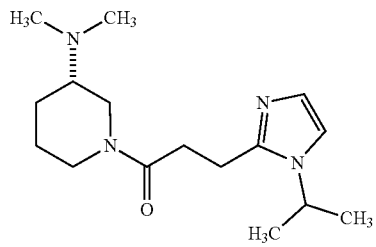 [SMILES: CC(C)n1ccnc1CCC(=O)N1CCC[C@H](N(C)C)C1]

Diisopropylethylamine (0.058 mL, 0.33 mmol), HBTU (0.0499 g, 0.132 mmol) and (S)-3-(dimethylamino)piperidine hydrochloride (0.0221 g, 0.110 mmol) were added to a solution of 3-(1-isopropyl-1H-imidazol-2-yl)propanoic acid (0.0200 g, 0.110 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain (S)-1-(3-(dimethylamino)piperidin-1-yl)-3-(1-isopropyl-1H-imidazol-2-yl)propan-1-one (0.0268 g, 0.0916 mmol, 84%)(hereinafter referred to as the compound of Example 5) as a colorless oil.

$^1$H-NMR (400 MHz, CDCl$_3$) δ: 1.39-1.44 (6H, m), 1.68-1.83 (3H, m), 1.98-2.60 (9H, m), 2.80-3.05 (5H, m), 3.84-4.09 (1H, m), 4.40-4.71 (2H, m), 6.89-6.96 (2H, m).

ESI-MS: m/z=293 (M+H)$^+$.

Example 6: Synthesis of (R)-1-(3-(dimethylamino)piperidin-1-yl)-3-(1-isopropyl-1H-imidazol-2-yl)propan-1-one

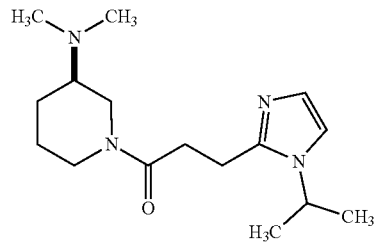 [SMILES: CC(C)n1ccnc1CCC(=O)N1CCC[C@@H](N(C)C)C1]

Diisopropylethylamine (0.173 mL, 0.988 mmol), HBTU (0.150 g, 0.395 mmol) and (R)-3-(dimethylamino)piperidine (0.0422 g, 0.329 mmol) were added to a solution of 3-(1-isopropyl-1H-imidazol-2-yl)propanoic acid (0.0600 g, 0.329 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain (R)-1-(3-(dimethylamino)piperidin-1-yl)-3-(1-isopropyl-1H-imidazol-2-yl)propan-1-one (0.0820 g, 0.280 mmol, 85%)(hereinafter referred to as the compound of Example 6) as a colorless oil.

$^1$H-NMR (400 MHz, CDCl$_3$) δ: 1.39-1.44 (6H, m), 1.68-1.83 (3H, m), 1.98-2.60 (9H, m), 2.80-3.05 (5H, m), 3.84-4.09 (1H, m), 4.40-4.71 (2H, m), 6.89-6.96 (2H, m).

ESI-MS: m/z=293 (M+H)$^+$.

Example 7: Synthesis of 1-(3-(dimethylamino)azetidin-1-yl)-3-(1-(2,2,2-trifluoroethyl)-1H-imidazol-2-yl)propan-1-one

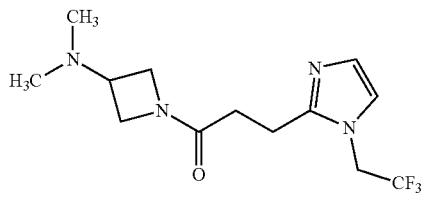 [SMILES: CN(C)C1CN(C(=O)CCc2nccn2CC(F)(F)F)C1]

Diisopropylethylamine (0.284 mL, 1.62 mmol), HBTU (0.246 g, 0.649 mmol) and 3-(dimethylamino)azetidine hydrochloride (0.0934 g, 0.540 mmol) were added to a solution of 3-(1-(2,2,2-trifluoroethyl)-1H-imidazol-2-yl)propanoic acid (0.120 g, 0.540 mmol) in chloroform (6.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain 1-(3-(dimethylamino)azetidin-1-yl)-3-(1-(2,2,2-trifluoroethyl)-1H-imidazol-2-yl)propan-1-one (0.150 g, 0.493 mmol, 91%)(hereinafter referred to as the compound of Example 7) as a colorless oil.

¹H-NMR (400 MHz, CDCl₃) δ: 2.16 (6H, s), 2.62-2.69 (2H, m), 2.93-3.10 (3H, m), 3.75-3.82 (1H, m), 3.92-3.98 (2H, m), 4.09-4.16 (1H, m), 4.56-4.68 (2H, m), 6.87-6.89 (1H, m), 6.98-7.00 (1H, m).

ESI-MS: m/z=305 (M+H)⁺.

Example 8: Synthesis of (R)-1-(3-(dimethylamino)piperidin-1-yl)-3-(1-(2,2,2-trifluoroethyl)-1H-imidazol-2-yl)propan-1-one

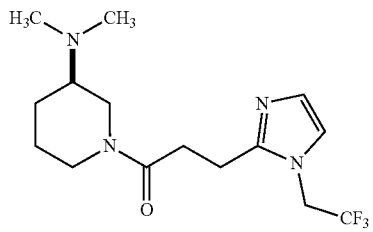 [SMILES: CN(C)[C@@H]1CCCN(C(=O)CCc2nccn2CC(F)(F)F)C1]

Diisopropylethylamine (0.142 mL, 0.810 mmol), HBTU (0.123 g, 0.324 mmol) and (R)-3-(dimethylamino)piperidine (0.0346 g, 0.270 mmol) were added to a solution of 3-(1-(2,2,2-trifluoroethyl)-1H-imidazol-2-yl)propanoic acid (0.0600 g, 0.270 mmol) in chloroform (3.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain (R)-1-(3-(dimethylamino)piperidin-1-yl)-3-(1-(2,2,2-trifluoroethyl)-1H-imidazol-2-yl)propan-1-one (0.0790 g, 0.238 mmol, 88%)(hereinafter referred to as the compound of Example 8) as a colorless oil.

¹H-NMR (400 MHz, CDCl₃) δ: 1.32-1.45 (2H, m), 1.65-1.85 (1H, m), 2.02-2.21 (2H, m), 2.29-2.31 (6H, m), 2.40-2.56 (1H, m), 2.78-3.00 (5H, m), 3.74-4.01 (1H, m), 4.38-4.75 (3H, m), 6.85-6.88 (1H, m), 6.96-6.98 (1H, m).

ESI-MS: m/z=333 (M+H)⁺.

Example 9: Synthesis of (R)-1-(3-(dimethylamino)piperidin-1-yl)-3-(1-(2-methoxyethyl)-1H-imidazol-2-yl)propan-1-one

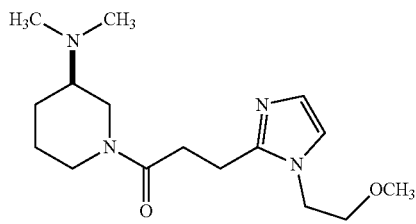 [SMILES: COCCn1ccnc1CCC(=O)N1CCC[C@@H](N(C)C)C1]

Diisopropylethylamine (0.222 mL, 1.27 mmol), HBTU (0.361 g, 0.953 mmol) and (R)-3-(dimethylamino)piperidine (0.0810 g, 0.635 mmol) were added to a solution of 3-(1-(2-methoxyethyl)-1H-imidazol-2-yl)propanoic acid (0.126 g, 0.635 mmol) in chloroform (6.4 mL) at room temperature. The reaction liquid was stirred at the same temperature for 15 hours. A saturated aqueous solution of potassium carbonate was added to the reaction liquid and the reaction liquid was extracted with chloroform. The organic layer was dried over anhydrous sodium sulfate and filtered and the filtrate was concentrated under reduced pressure. The residue was purified by column chromatography (NH silica gel, chloroform/methanol) to obtain (R)-1-(3-(dimethylamino)piperidin-1-yl)-3-(1-(2-methoxyethyl)-1H-imidazol-2-yl)propan-1-one (0.165 g, 0.536 mmol, 84%)(hereinafter referred to as the compound of Example 9) as a colorless oil.

¹H-NMR (400 MHz, CDCl₃) δ: 1.37-1.45 (2H, m), 1.75-1.81 (1H, m), 2.00-2.20 (2H, m), 2.31-2.33 (6H, m), 2.43-2.57 (1H, m), 2.81-3.02 (5H, m), 3.32 (3H, s), 3.59-3.62 (2H, m), 3.84-4.11 (3H, m), 4.49-4.69 (1H, m), 6.89-6.93 (2H, m).

ESI-MS: m/z=309 (M+H)⁺.

Example 10: Synthesis of 3-(5-chloro-1-methyl-1H-imidazol-2-yl)-1-(3-(dimethylamino)azetidin-1-yl)propan-1-one

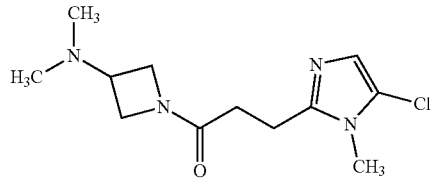 [SMILES: CN(C)C1CN(C(=O)CCc2ncc(Cl)n2C)C1]

Diisopropylethylamine (0.146 mL, 0.834 mmol), HBTU (0.158 g, 0.417 mmol) and 3-(dimethylamino)azetidine hydrochloride (0.0457 g, 0.264 mmol) were added to a solution of 3-(5-chloro-1-methyl-1H-imidazol-2-yl)propanoic acid (0.0524 g, 0.278 mmol) in chloroform (2.8 mL) at room temperature. The reaction liquid was stirred at the same temperature for 16 hours. A saturated aqueous solution of potassium carbonate was added to the reaction liquid and the reaction liquid was extracted with chloroform. The organic layer was dried over anhydrous sodium sulfate and filtered and the filtrate was concentrated under reduced pressure. The residue was purified by column chromatography (NH silica gel, ethyl acetate/methanol) to obtain 3-(5-chloro-1-methyl-1H-imidazol-2-yl)-1-(3-(dimethylamino)azetidin-1-yl)propan-1-one (0.0656 g, 0.242 mmol, 87%)(hereinafter referred to as the compound of Example 10) as a white solid.

¹H-NMR (400 MHz, CDCl₃) δ: 2.17 (6H, s), 2.56-2.69 (2H, m), 2.87-3.00 (2H, m), 3.03-3.09 (3H, m), 3.53 (3H, s), 3.81 (1H, dd, J=9.9, 5.2 Hz), 3.95-4.01 (2H, m), 4.13-4.17 (1H, m), 6.83 (1H, s).

ESI-MS: m/z=271 (M+H)⁺.

Example 11: Synthesis of (S)-3-(5-chloro-1-methyl-1H-imidazol-2-yl)-1-(3-(dimethylamino)piperidin-1-yl)propan-1-one

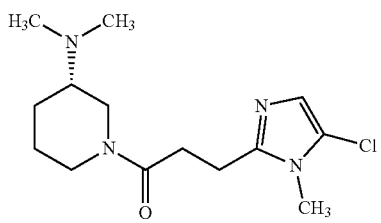 [SMILES: CN(C)[C@H]1CCCN(C(=O)CCc2ncc(Cl)n2C)C1]

Diisopropylethylamine (0.233 mL, 1.34 mmol), HBTU (0.253 g, 0.668 mmol) and (S)-3-(dimethylamino)piperidine hydrochloride (0.0900 g, 0.445 mmol) were added to a solution of 3-(5-chloro-1-methyl-1H-imidazol-2-yl)propanoic acid (0.0840 g, 0.445 mmol) in chloroform (5.0 mL) at room temperature. The reaction liquid was stirred at the same temperature for 16 hours. A saturated aqueous solution of sodium hydrogencarbonate was added to the reaction liquid and the reaction liquid was extracted with chloroform. The organic layer was washed with a 10% aqueous solution of sodium chloride, dried over anhydrous sodium sulfate and filtered. The filtrate was concentrated under reduced pressure. The residue was purified by column chromatography (NH silica gel, chloroform/methanol) to obtain (S)-3-(5-chloro-1-methyl-1H-imidazol-2-yl)-1-(3-(dimethylamino)piperidin-1-yl)propan-1-one (0.0800 g, 0.268 mmol, 60%) (hereinafter referred to as the compound of Example 11) as a colorless oil.

$^1$H-NMR (400 MHz, CDCl$_3$) δ: 1.30-1.48 (2H, m), 1.68-1.84 (1H, m), 1.92-2.22 (2H, m), 2.28-2.31 (6H, m), 2.40-2.58 (1H, m), 2.77-3.00 (5H, m), 3.51-3.54 (3H, m), 3.75-4.02 (1H, m), 4.42-4.64 (1H, m), 6.80 (1H, s).

ESI-MS: m/z=299 (M+H)$^+$.

Example 12: Synthesis of (R)-3-(5-chloro-1-methyl-1H-imidazol-2-yl)-1-(3-(dimethylamino)piperidin-1-yl)propan-1-one

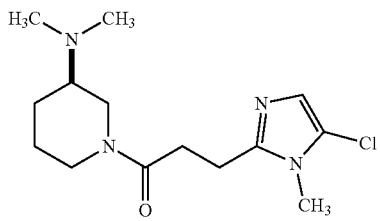 [SMILES: CN(C)[C@@H]1CCCN(C(=O)CCc2ncc(Cl)n2C)C1]

Diisopropylethylamine (0.0863 mL, 0.494 mmol), HBTU (0.141 g, 0.371 mmol) and (R)-3-(dimethylamino)piperidine (0.0301 g, 0.235 mmol) were added to a solution of 3-(5-chloro-1-methyl-1H-imidazol-2-yl)propanoic acid (0.0466 g, 0.247 mmol) in chloroform (2.5 mL) at room temperature. The reaction liquid was stirred at the same temperature for 16 hours. A saturated aqueous solution of potassium carbonate was added to the reaction liquid and the reaction liquid was extracted with chloroform. The organic layer was dried over anhydrous sodium sulfate and filtered and the filtrate was concentrated under reduced pressure. The residue was purified by column chromatography (NH silica gel, ethyl acetate/methanol) to obtain (R)-3-(5-chloro-1-methyl-1H-imidazol-2-yl)-1-(3-(dimethylamino)piperidin-1-yl)propan-1-one (0.0585 g, 0.196 mmol, 79%)(hereinafter referred to as the compound of Example 12) as a white solid.

$^1$H-NMR (400 MHz, CDCl$_3$) δ: 1.30-1.48 (2H, m), 1.68-1.84 (1H, m), 1.92-2.22 (2H, m), 2.28-2.31 (6H, m), 2.40-2.58 (1H, m), 2.77-3.00 (5H, m), 3.51-3.54 (3H, m), 3.75-4.02 (1H, m), 4.42-4.64 (1H, m), 6.80 (1H, s).

ESI-MS: m/z=299 (M+H)$^+$.

Example 13: Synthesis of 1-(3-(dimethylamino)azetidin-1-yl)-3-(1-methyl-1H-imidazol-2-yl)-propan-1-one Hydrochloride

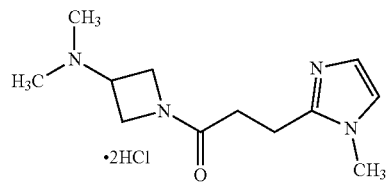 [SMILES: CN(C)C1CN(C(=O)CCc2nccn2C)C1]

A solution of hydrogen chloride in diethyl ether (2.0 N, 0.391 mL, 0.781 mmol) was added to a solution of 1-(3-(dimethylamino)azetidin-1-yl)-3-(1-methyl-1H-imidazol-2-yl)-propan-1-one (0.0710 g, 0.300 mmol) in diethyl ether (3.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain 1-(3-(dimethylamino)azetidin-1-yl)-3-(1-methyl-1H-imidazol-2-yl)-propan-1-one hydrochloride (0.0831 g, 0.269 mmol, 90%)(hereinafter referred to as the compound of Example 13) as a white solid.

$^1$H-NMR (400 MHz, D$_2$O) δ: 2.74-2.80 (2H, m), 2.89 (6H, s), 3.21-3.28 (2H, m), 3.82 (3H, s), 4.12-4.28 (2H, m), 4.32-4.50 (2H, m), 4.57-4.66 (1H, m), 7.28-7.36 (2H, m).

ESI-MS: as 1-(3-(dimethylamino)azetidin-1-yl)-3-(1-methyl-1H-imidazol-2-yl)-propan-1-one: m/z=237 (M+H)$^+$.

Example 14: Synthesis of (S)-1-(3-(dimethylamino)piperidin-1-yl)-3-(1-methyl-1H-imidazol-2-yl)propan-1-one Hydrochloride

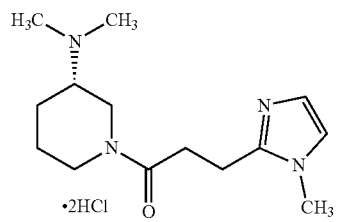 [SMILES: CN(C)[C@H]1CCCN(C(=O)CCc2nccn2C)C1]

A solution of hydrogen chloride in diethyl ether (2.0 N, 0.423 mL, 0.846 mmol) was added to a solution of (S)-1-(3-(dimethylamino)piperidin-1-yl)-3-(1-methyl-1H-imidazol-2-yl)propan-1-one (0.0860 g, 0.325 mmol) in diethyl ether (3.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain (S)-1-(3-(dimethylamino)piperidin-1-yl)-3-(1-methyl-1H-imidazol-2-yl)propan-1-one hydrochloride (0.0576 g, 0.171 mmol, 53%)(hereinafter referred to as the compound of Example 14) as a white solid.

$^1$H-NMR (400 MHz, D$_2$O) δ: 1.60-1.73 (1H, m), 1.85-1.98 (2H, m), 2.15-2.30 (1H, m), 2.92-3.09 (8H, m), 3.20-3.44 (5H, m), 3.70-3.80 (1H, m), 3.83 (3H, s), 4.15-4.35 (1H, m), 7.27-7.33 (2H, m).

ESI-MS: as (S)-1-(3-(dimethylamino)piperidin-1-yl)-3-(1-methyl-1H-imidazol-2-yl)propan-1-one: m/z=265 (M+H)$^+$.

Example 15: Synthesis of (R)-1-(3-(dimethylamino)piperidin-1-yl)-3-(1-methyl-1H-imidazol-2-yl)propan-1-one Hydrochloride

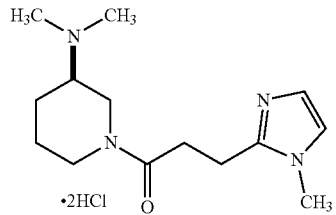 [SMILES: CN(C)[C@@H]1CCCN(C(=O)CCc2nccn2C)C1]

A solution of hydrogen chloride in diethyl ether (2.0 N, 0.281 mL, 0.562 mmol) was added to a solution of (R)-1-(3-(dimethylamino)piperidin-1-yl)-3-(1-methyl-1H-imidazol-2-yl)propan-1-one (0.0594 g, 0.225 mmol) in diethyl ether (2.3 mL) at 0° C. The reaction liquid was stirred at the same temperature for 1 hour and then stirred at room temperature for 1 hour. The white solid precipitated was filtered and collected, washed with diethyl ether and dried at room temperature to obtain (R)-1-(3-(dimethylamino)piperidin-1-yl)-3-(1-methyl-1H-imidazol-2-yl)propan-1-one hydrochloride (0.0492 g, 0.146 mmol, 65%)(hereinafter referred to as the compound of Example 15) as a white solid.

$^1$H-NMR (400 MHz, D$_2$O) δ: 1.60-1.73 (1H, m), 1.85-1.98 (2H, m), 2.15-2.30 (1H, m), 2.92-3.09 (8H, m), 3.20-3.44 (5H, m), 3.70-3.80 (1H, m), 3.83 (3H, s), 4.15-4.35 (1H, m), 7.27-7.33 (2H, m).

ESI-MS: as (R)-1-(3-(dimethylamino)piperidin-1-yl)-3-(1-methyl-1H-imidazol-2-yl)propan-1-one: m/z=265 (M+H)$^+$.

Example 16: Synthesis of 1-(3-(dimethylamino)azetidin-1-yl)-3-(1-isopropyl-1H-imidazol-2-yl)propan-1-one Hydrochloride

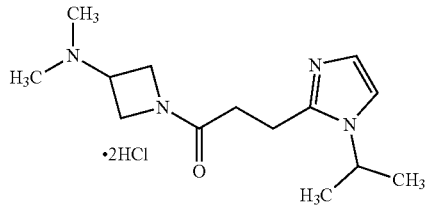 [SMILES: CC(C)n1ccnc1CCC(=O)N1CC(N(C)C)C1]

A solution of hydrogen chloride in diethyl ether (2.0 N, 0.393 mL, 0.787 mmol) was added to a solution of 1-(3-(dimethylamino)azetidin-1-yl)-3-(1-isopropyl-1H-imidazol-2-yl)propan-1-one (0.0820 g, 0.310 mmol) in diethyl ether (3.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain 1-(3-(dimethyl amino)azetidin-1-yl)-3-(1-isopropyl-1H-imidazol-2-yl)propan-1-one hydrochloride (0.0942 g, 0.279 mmol, 90%)(hereinafter referred to as the compound of Example 16) as a white solid.

$^1$H-NMR (400 MHz, D$_2$O) δ: 1.47-1.51 (6H, m), 2.74-2.80 (2H, m), 2.88 (6H, s), 3.24-3.30 (2H, m), 4.13-4.24 (2H, m), 4.33-4.48 (2H, m), 4.58-4.74 (2H, m), 7.36-7.38 (1H, m), 7.49-7.51 (1H, m).

ESI-MS: as 1-(3-(dimethylamino)azetidin-1-yl)-3-(1-isopropyl-1H-imidazol-2-yl)propan-1-one: m/z=265 (M+H)$^+$.

Example 17: Synthesis of (S)-1-(3-(dimethylamino)piperidin-1-yl)-3-(1-isopropyl-1H-imidazol-2-yl)propan-1-one Hydrochloride

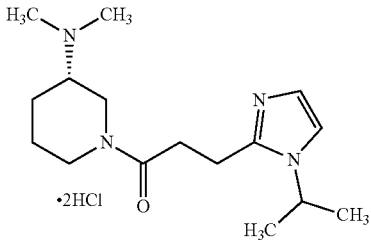 [SMILES: CC(C)n1ccnc1CCC(=O)N1CCC[C@H](N(C)C)C1]

A solution of hydrogen chloride in diethyl ether (2.0 N, 0.401 mL, 0.801 mmol) was added to a solution of (S)-1-(3-(dimethylamino)piperidin-1-yl)-3-(1-isopropyl-1H-imidazol-2-yl)propan-1-one (0.0900 g, 0.308 mmol) in diethyl ether (3.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain (S)-1-(3-(dimethylamino)piperidin-1-yl)-3-(1-isopropyl-1H-imidazol-2-yl)propan-1-one hydrochloride (0.0840 g, 0.230 mmol, 75%)(hereinafter referred to as the compound of Example 17) as a white solid.

$^1$H-NMR (400 MHz, D$_2$O) δ: 1.48-1.70 (8H, m), 1.86-1.98 (2H, m), 2.12-2.28 (1H, m), 2.89-3.12 (8H, m), 3.24-3.45 (5H, m), 3.71-3.82 (1H, m), 4.14-4.36 (1H, m), 7.35 (1H, brs), 7.50 (1H, brs).

ESI-MS: as (S)-1-(3-(dimethylamino)piperidin-1-yl)-3-(1-isopropyl-1H-imidazol-2-yl)propan-1-one: m/z=293 (M+H)$^+$.

Example 18: Synthesis of (R)-1-(3-(dimethylamino)piperidin-1-yl)-3-(1-isopropyl-1H-imidazol-2-yl)propan-1-one Hydrochloride

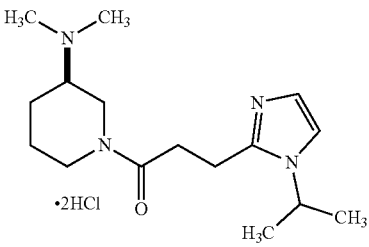 [SMILES: CC(C)n1ccnc1CCC(=O)N1CCC[C@@H](N(C)C)C1]

A solution of hydrogen chloride in diethyl ether (2.0 N, 0.365 mL, 0.730 mmol) was added to a solution of (R)-1-(3-(dimethylamino)piperidin-1-yl)-3-(1-isopropyl-1H-imidazol-2-yl)propan-1-one (0.0820 g, 0.280 mmol) in diethyl ether (3.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain (R)-1-(3-(dimethylamino)piperidin-1-yl)-3-(1-isopropyl-1H-imidazol-2-yl)propan-1-one hydrochloride (0.0625 g, 0.171 mmol, 61%)(hereinafter referred to as the compound of Example 18) as a white solid.

¹H-NMR (400 MHz, D₂O) δ: 1.48-1.70 (8H, m), 1.86-1.98 (2H, m), 2.12-2.28 (1H, m), 2.89-3.12 (8H, m), 3.24-3.45 (5H, m), 3.71-3.82 (1H, m), 4.14-4.36 (1H, m), 7.35 (1H, brs), 7.50 (1H, brs).

ESI-MS: as (R)-1-(3-(dimethylamino)piperidin-1-yl)-3-(1-isopropyl-1H-imidazol-2-yl)propan-1-one: m/z=293 (M+H)⁺.

Example 19: Synthesis of 1-(3-(dimethylamino)azetidin-1-yl)-3-(1-(2,2,2-trifluoroethyl)-1H-imidazol-2-yl)propan-1-one Hydrochloride

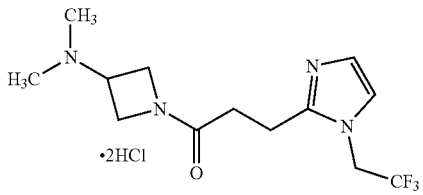 [SMILES: CN(C)C1CN(C(=O)CCc2nccn2CC(F)(F)F)C1]

A solution of hydrogen chloride in diethyl ether (2.0 N, 0.650 mL, 1.30 mmol) was added to a solution of 1-(3-(dimethylamino)azetidin-1-yl)-3-(1-(2,2,2-trifluoroethyl)-1H-imidazol-2-yl)propan-1-one (0.150 g, 0.493 mmol) in diethyl ether (6.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain 1-(3-(dimethylamino)azetidin-1-yl)-3-(1-(2,2,2-trifluoroethyl)-1H-imidazol-2-yl)propan-1-one hydrochloride (0.137 g, 0.363 mmol, 74%)(hereinafter referred to as the compound of Example 19) as a white solid.

¹H-NMR (400 MHz, D₂O) δ: 2.77-2.84 (2H, m), 2.89 (6H, s), 3.27-3.33 (2H, m), 4.13-4.26 (2H, m), 4.32-4.47 (2H, m), 4.57-4.64 (1H, m), 5.08-5.16 (2H, m), 7.42-7.46 (1H, m), 7.51-7.55 (1H, m).

ESI-MS: as 1-(3-(dimethylamino)azetidin-1-yl)-3-(1-(2,2,2-trifluoroethyl)-1H-imidazol-2-yl)propan-1-one: m/z=305 (M+H)⁺.

Example 20: Synthesis of (R)-1-(3-(dimethylamino)piperidin-1-yl)-3-(1-(2,2,2-trifluoroethyl)-1H-imidazol-2-yl)propan-1-one Hydrochloride

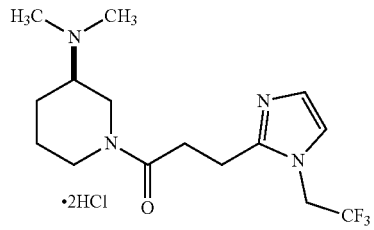 [SMILES: CN(C)[C@@H]1CCCN(C(=O)CCc2nccn2CC(F)(F)F)C1]

A solution of hydrogen chloride in diethyl ether (2.0 N, 0.309 mL, 0.618 mmol) was added to a solution of (R)-1-(3-(dimethylamino)piperidin-1-yl)-3-(1-(2,2,2-trifluoroethyl)-1H-imidazol-2-yl)propan-1-one (0.0790 g, 0.238 mmol) in diethyl ether (3.0 mL) at 0° C. The reaction liquid was stirred at the same temperature for 1 hour and then stirred at room temperature for 30 minutes. The white solid precipitated was filtered and collected, washed with diethyl ether and dried at room temperature to obtain (R)-1-(3-(dimethylamino)piperidin-1-yl)-3-(1-(2,2,2-trifluoroethyl)-1H-imidazol-2-yl)propan-1-one hydrochloride (0.0349 g, 0.0861 mmol, 36%)(hereinafter referred to as the compound of Example 20) as a white solid.

¹H-NMR (400 MHz, D₂O) δ: 1.42-1.70 (1H, m), 1.83-1.94 (2H, m), 2.12-2.27 (1H, m), 2.87-2.94 (6H, m), 3.04-3.14 (2H, m), 3.23-3.42 (5H, m), 3.70-3.78 (1H, m), 4.12-4.32 (1H, m), 5.10-5.18 (2H, m), 7.43-7.45 (1H, m), 7.52-7.54 (1H, m).

ESI-MS: as (R)-1-(3-(dimethylamino)piperidin-1-yl)-3-(1-(2,2,2-trifluoroethyl)-1H-imidazol-2-yl)propan-1-one: m/z=333 (M+H)⁺.

Example 21: Synthesis of (R)-1-(3-(dimethylamino)piperidin-1-yl)-3-(1-(2-methoxyethyl)-1H-imidazol-2-yl)propan-1-one Hydrochloride

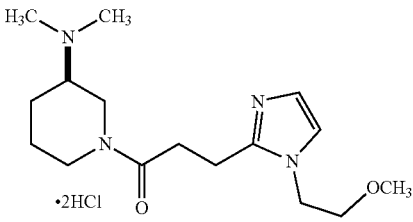 [SMILES: COCCn1ccnc1CCC(=O)N1CCC[C@@H](N(C)C)C1]

A solution of hydrogen chloride in diethyl ether (2.0 N, 0.670 mL, 1.34 mmol) was added to a solution of (R)-1-(3-(dimethylamino)piperidin-1-yl)-3-(1-(2-methoxyethyl)-1H-imidazol-2-yl)propan-1-one (0.165 g, 0.536 mmol) in diethyl ether (10.7 mL) at 0° C. The reaction liquid was stirred at the same temperature for 1 hour and then stirred at room temperature for 3 hours. The white solid precipitated was filtered and collected, washed with diethyl ether and dried at room temperature to obtain (R)-1-(3-(dimethylamino)piperidin-1-yl)-3-(1-(2-methoxyethyl)-1H-imidazol-2-yl)propan-1-one hydrochloride (0.177 g, 0.463 mmol, 86%)(hereinafter referred to as the compound of Example 21) as a white solid.

$^1$H-NMR (400 MHz, D$_2$O) δ: 1.44-1.68 (1H, m), 1.74-1.93 (2H, m), 2.16-2.24 (1H, m), 2.89-2.93 (6H, m), 3.00-3.08 (2H, m), 3.23-3.41 (8H, m), 3.70-3.76 (1H, m), 3.82-3.85 (2H, m), 4.14-4.30 (1H, m), 4.36-4.38 (2H, m), 7.33-7.34 (1H, m), 7.40-7.42 (1H, m).

ESI-MS: as (R)-1-(3-(dimethylamino)piperidin-1-yl)-3-(1-(2-methoxyethyl)-1H-imidazol-2-yl)propan-1-one: m/z=309 (M+H)$^+$.

Example 22: Synthesis of 3-(5-chloro-1-methyl-1H-imidazol-2-yl)-1-(3-(dimethylamino)azetidin-1-yl)propan-1-one Hydrochloride

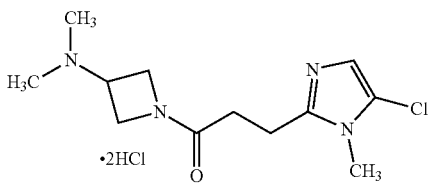 [SMILES: CN(C)C1CN(C(=O)CCc2ncc(Cl)n2C)C1]

A solution of hydrogen chloride in diethyl ether (2.0 N, 0.302 mL, 0.605 mmol) was added to a solution of 3-(5-chloro-1-methyl-1H-imidazol-2-yl)-1-(3-(dimethylamino)azetidin-1-yl)propan-1-one (0.0655 g, 0.242 mmol) in diethyl ether (4.8 mL) at 0° C. The reaction liquid was stirred at the same temperature for 1 hour and then stirred at room temperature for 1 hour. The white solid precipitated was filtered and collected, washed with diethyl ether and dried at room temperature to obtain 3-(5-chloro-1-methyl-1H-imidazol-2-yl)-1-(3-(dimethylamino)azetidin-1-yl)propan-1-one hydrochloride (0.064 g, 0.186 mmol, 77%)(hereinafter referred to as the compound of Example 22) as a white solid.

$^1$H-NMR (400 MHz, D$_2$O) δ: 2.78 (2H, t, J=7.1 Hz), 2.92 (6H, s), 3.26 (2H, t, J=7.1 Hz), 3.77 (3H, s), 4.17-4.28 (2H, m), 4.37-4.41 (1H, m), 4.45-4.48 (1H, m), 4.61-4.66 (1H, m), 7.44 (1H, s).

ESI-MS: as 3-(5-chloro-1-methyl-1H-imidazol-2-yl)-1-(3-(dimethylamino)azetidin-1-yl)propan-1-one: m/z=271 (M+H)$^+$.

Example 23: Synthesis of (S)-3-(5-chloro-1-methyl-1H-imidazol-2-yl)-1-(3-(dimethylamino)piperidin-1-yl)propan-1-one Hydrochloride

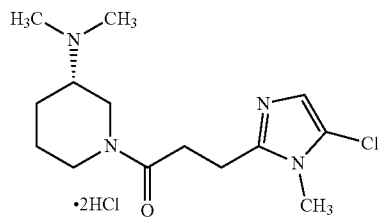 [SMILES: CN(C)[C@H]1CCCN(C(=O)CCc2ncc(Cl)n2C)C1]

A solution of hydrogen chloride in diethyl ether (2.0 N, 0.348 mL, 0.696 mmol) was added to a solution of (S)-3-(5-chloro-1-methyl-1H-imidazol-2-yl)-1-(3-(dimethylamino)piperidin-1-yl)propan-1-one (0.0800 g, 0.268 mmol) in diethyl ether (1.0 mL) at 0° C. The reaction liquid was stirred at the same temperature for 1 hour and then stirred at room temperature for 30 minutes. The white solid precipitated was filtered and collected, washed with diethyl ether (3.0 mL) and dried at room temperature for 36 hours to obtain (S)-3-(5-chloro-1-methyl-1H-imidazol-2-yl)-1-(3-(dimethylamino)piperidin-1-yl)propan-1-one hydrochloride (0.0512 g, 0.138 mmol, 51%)(hereinafter referred to as the compound of Example 23) as a white solid.

$^1$H-NMR (400 MHz, D$_2$O) δ: 1.60-1.71 (1H, m), 1.78-1.96 (2H, m), 2.14-2.28 (1H, m), 2.89-2.96 (6H, m), 3.01-3.10 (2H, m), 3.23-3.44 (5H, m), 3.70-3.80 (4H, m), 4.20-4.33 (1H, m), 7.43 (1H, s).

ESI-MS: as (S)-3-(5-chloro-1-methyl-1H-imidazol-2-yl)-1-(3-(dimethylamino)piperidin-1-yl)propan-1-one: m/z=299 (M+H)$^+$.

Example 24: Synthesis of (R)-3-(5-chloro-1-methyl-1H-imidazol-2-yl)-1-(3-(dimethylamino)piperidin-1-yl)propan-1-one Hydrochloride

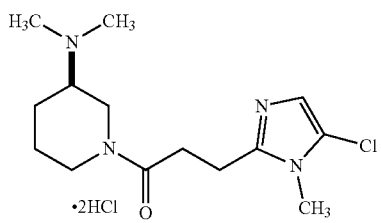 [SMILES: CN(C)[C@@H]1CCCN(C(=O)CCc2ncc(Cl)n2C)C1]

A solution of hydrogen chloride in diethyl ether (2.0 N, 0.245 mL, 0.489 mmol) was added to a solution of (R)-3-(5-chloro-1-methyl-1H-imidazol-2-yl)-1-(3-(dimethylamino)piperidin-1-yl)propan-1-one (0.0585 g, 0.196 mmol) in diethyl ether (3.9 mL) at 0° C. The reaction liquid was stirred at the same temperature for 1 hour and then stirred at room temperature for 1 hour. The white solid precipitated was filtered and collected, washed with diethyl ether and dried at room temperature to obtain (R)-3-(5-chloro-1-methyl-1H-imidazol-2-yl)-1-(3-(dimethylamino)piperidin-1-yl)propan-1-one hydrochloride (0.0644 g, 0.173 mmol, 88%)(hereinafter referred to as the compound of Example 24) as a white solid.

$^1$H-NMR (400 MHz, D$_2$O) δ: 1.60-1.71 (1H, m), 1.78-1.96 (2H, m), 2.14-2.28 (1H, m), 2.89-2.96 (6H, m), 3.01-3.10 (2H, m), 3.23-3.44 (5H, m), 3.70-3.80 (4H, m), 4.20-4.33 (1H, m), 7.43 (1H, s).

ESI-MS: as (R)-3-(5-chloro-1-methyl-1H-imidazol-2-yl)-1-(3-(dimethylamino)piperidin-1-yl)propan-1-one: m/z=299 (M+H)$^+$.

Example 25: Effect on Mouse Partial Sciatic Nerve Ligation Model

Using a partial sciatic nerve ligation model (Seltzer model) in mice by which neuropathic pain can be evaluated, the analgesic action of a cyclic amine derivative (I) or a pharmacologically acceptable salt thereof was investigated.
1. Experimental Method The mouse partial sciatic nerve ligation model was prepared in accordance with the method of Seltzer et al. (Malmberg et al., Pain, vol. 76, p. 215-222, 1998).

Slc: ICR mice (5 weeks old, male; from Japan SLC, Inc.) was anesthetized with sodium pentobarbital (70 mg/kg, intraperitoneal administration). The sciatic nerve at the femoral region of the right hind paw of each mouse was exposed and triply ligated tightly with silk suture of 8-0

(from NATSUME SEISAKUSHO CO., LTD.) under a stereomicroscope so that only half thickness of the nerve was trapped in the ligature. A group of mice thus treated was designated as a partial sciatic nerve ligation group. A group of mice whose sciatic nerve was just exposed and not ligated was designated as a sham surgery group.

Evaluation of neuropathic pain (hereinafter referred to as von Frey test) was performed as follows. Mice were conditioned for at least one hour in an acrylic cage for measurement (from NATSUME SEISAKUSHO CO. LTD.) placed on a wire net. Thereafter, using a filament (from North Coast Medical) which exerted a pressure of 0.16 g, the mice were subjected to mechanical tactile stimulus by applying the filament to the plantar surface of the right hind paw 3 times, each for 3 seconds, with an interval of 3 seconds. The withdrawal response observed during each mechanical tactile stimulus was scored (0, no response; 1, showed slow and/or slight withdrawal response in response to the stimulation; 2, showed quick withdrawal response without flinching (shaking paws quickly and continuously) nor licking (licking paws) in response to the stimulation; 3, showed quick withdrawal response with flinching and/or licking), and the sum of the scores obtained in the triplicate trials (hereinafter referred to as the total score) were used as a pain index.

Seven days after the sciatic nerve ligation surgery, the compounds of Examples 13 to 24 (0.3 to 10 mg/kg for the compounds of Examples 13 to 15 and 22 to 24 and 10 mg/kg for the compounds of Examples 16 to 21) or pregabalin as a positive control (10 mg/kg; Bosche Scientific) was dissolved in distilled water and orally administered to mice of the partial sciatic nerve ligation group. The partial sciatic nerve ligation mouse groups to which the compounds of Examples 13 to 24 were separately administered, were designated as a "partial sciatic nerve ligation+the compound of Example 13" group; a "partial sciatic nerve ligation+the compound of Example 14" group; a "partial sciatic nerve ligation+the compound of Example 15" group; a "partial sciatic nerve ligation+the compound of Example 16" group; a "partial sciatic nerve ligation+the compound of Example 17" group; a "partial sciatic nerve ligation+the compound of Example 18" group; a "partial sciatic nerve ligation+the compound of Example 19" group; a "partial sciatic nerve ligation+the compound of Example 20" group; a "partial sciatic nerve ligation+the compound of Example 21" group; a "partial sciatic nerve ligation+the compound of Example 22" group; a "partial sciatic nerve ligation+the compound of Example 23" group; and a "partial sciatic nerve ligation+the compound of Example 24" group, respectively. The partial sciatic nerve ligation mouse group to which pregabalin was administered, was designated as a "partial sciatic nerve ligation+pregabalin" group. A group wherein distilled water was orally administered to the mice of the partial sciatic nerve ligation group was designated as a "partial sciatic nerve ligation+distilled water" group. A group wherein distilled water was orally administered to the mice of the sham surgery group was designated as a "sham surgery+distilled water" group.

The von Frey test was carried out before oral administration of a test compound (pre-value), one hour, two hours, and three hours after the oral administration of a test compound.

2. Results

Figure 2:
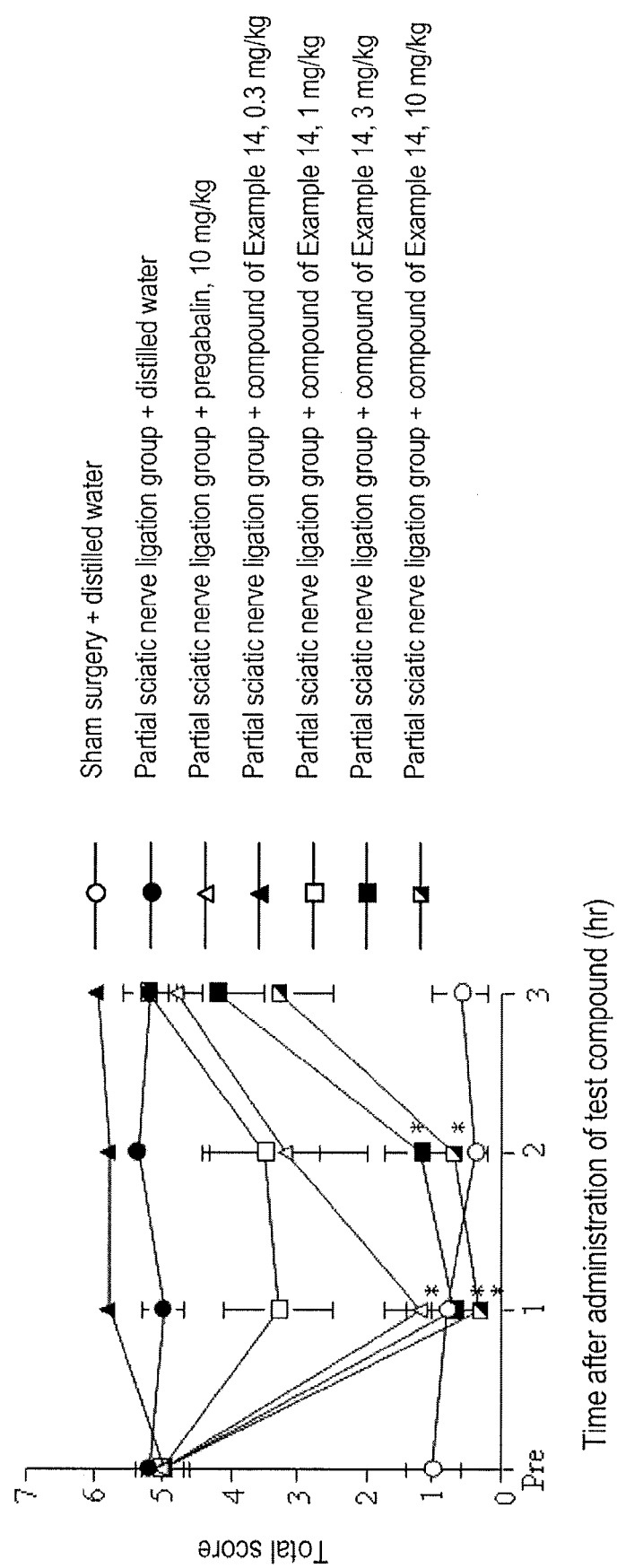
FIG. 2 is a graph showing the effect of the compound of Example 14 in a mouse partial sciatic nerve ligation model (oral administration).
Figure 3:
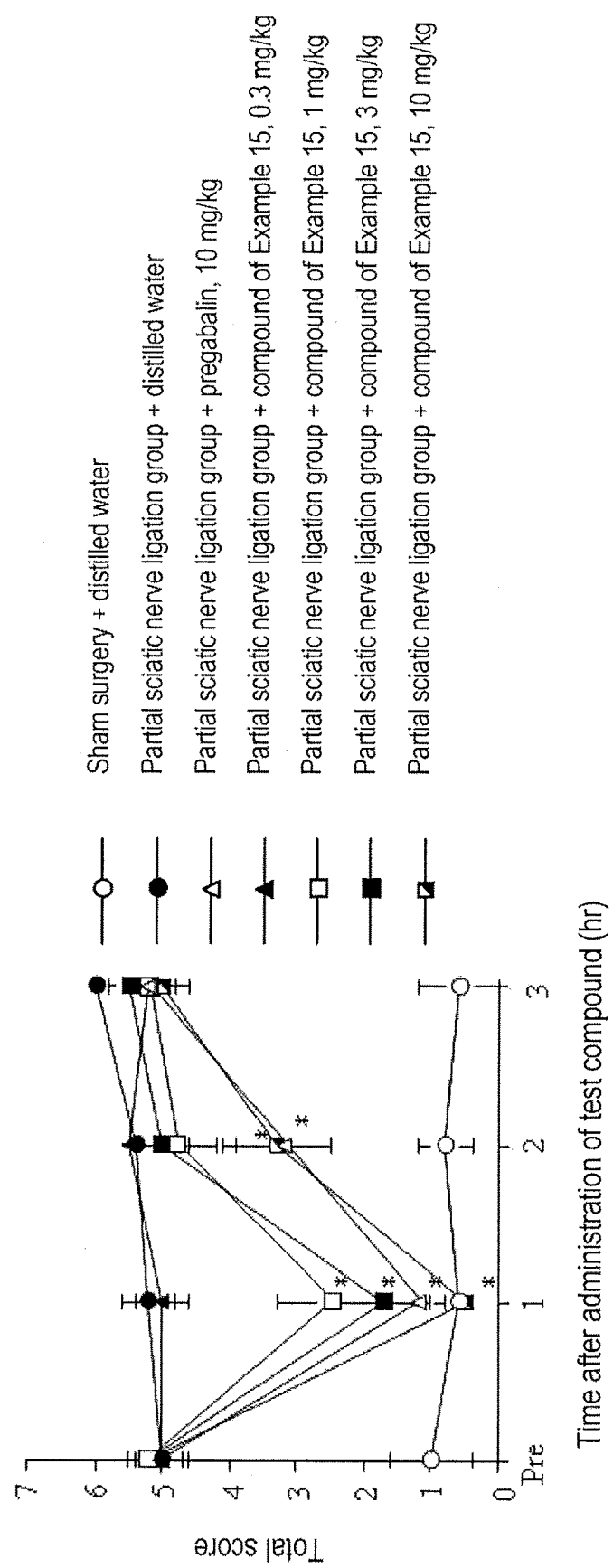
FIG. 3 is a graph showing the effect of the compound of Example 15 in a mouse partial sciatic nerve ligation model (oral administration).
Figure 4:
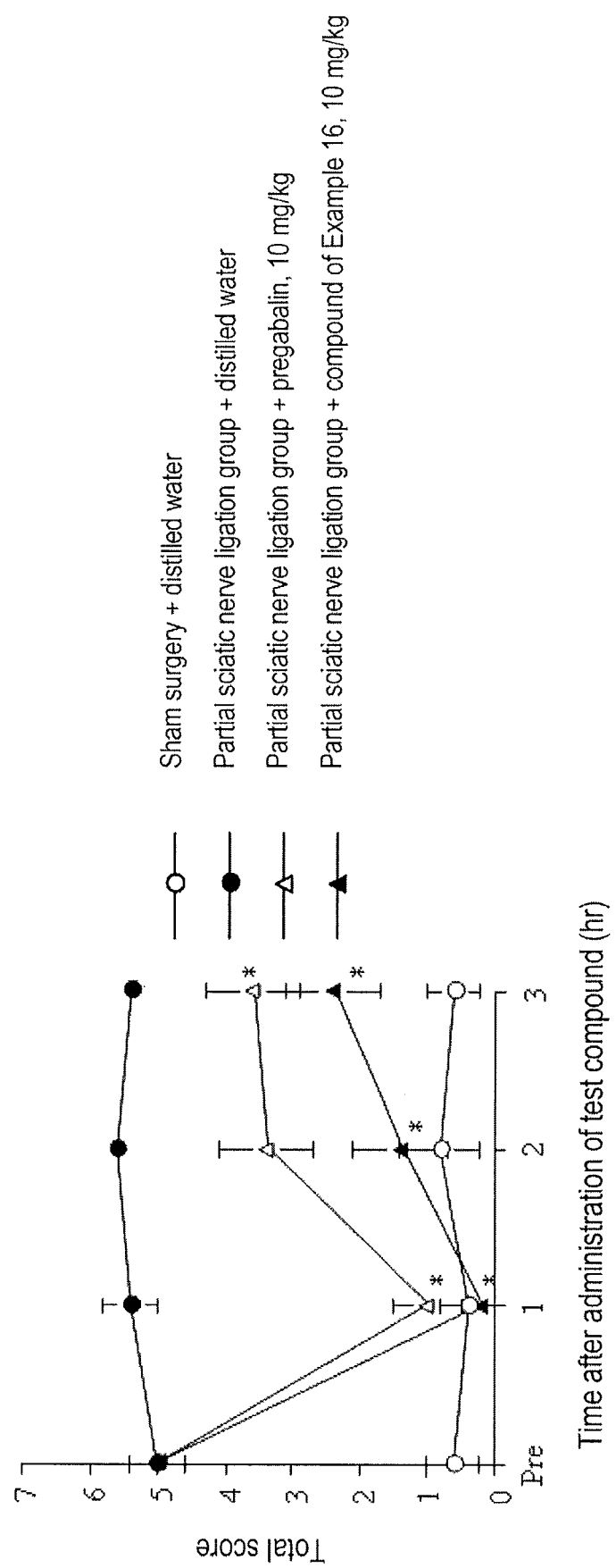
FIG. 4 is a graph showing the effect of the compound of Example 16 in a mouse partial sciatic nerve ligation model (oral administration).
Figure 5:
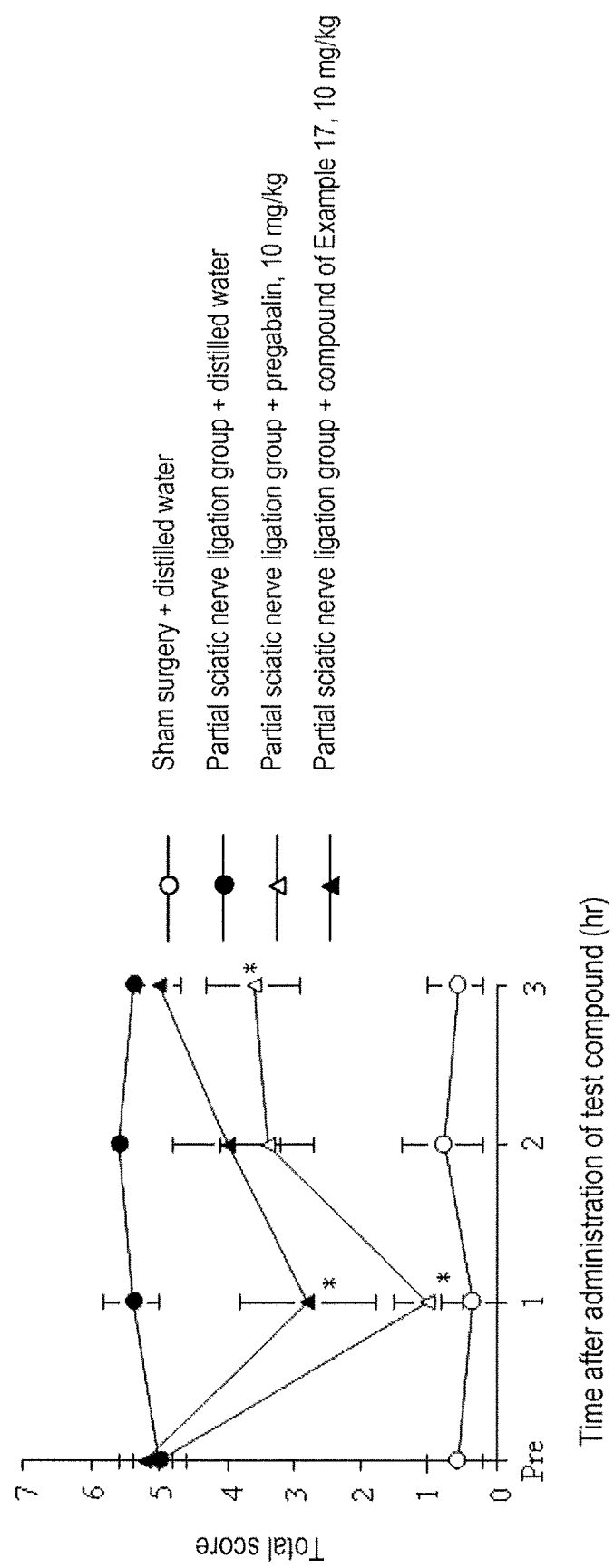
FIG. 5 is a graph showing the effect of the compound of Example 17 in a mouse partial sciatic nerve ligation model (oral administration).
Figure 6:
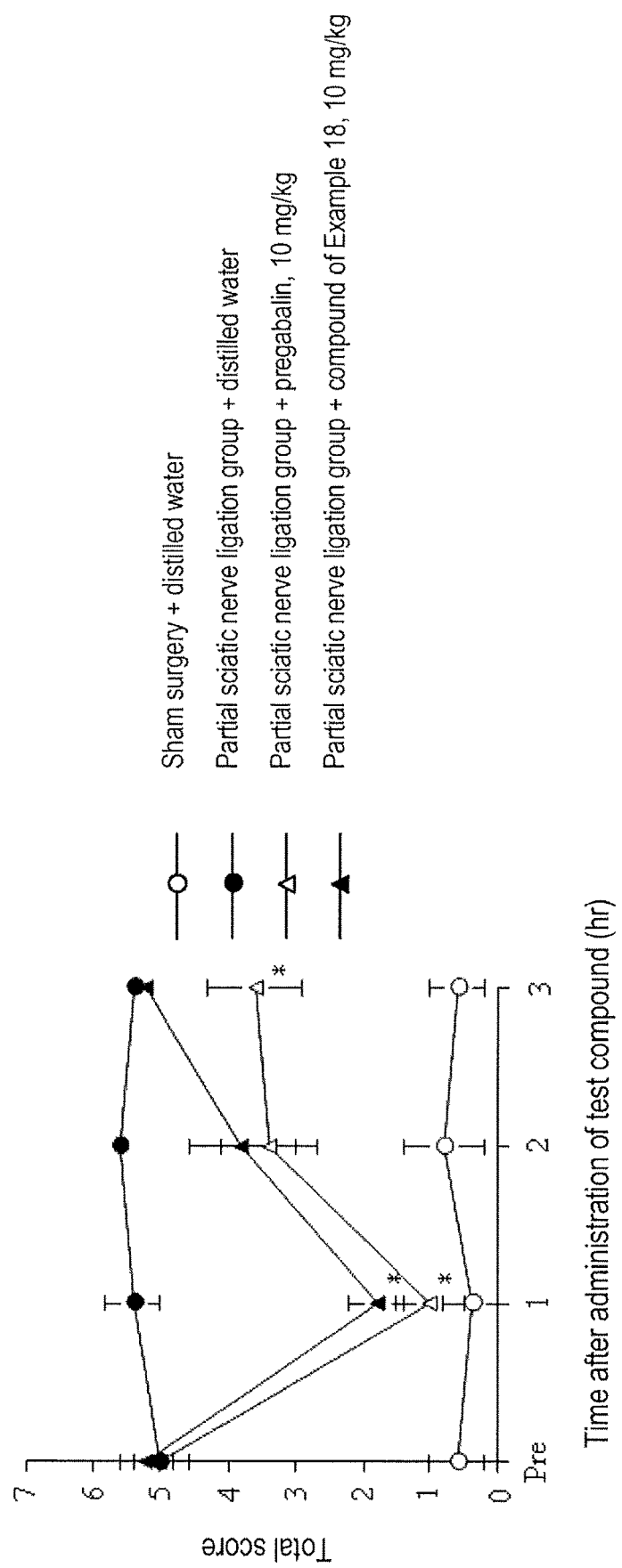
FIG. 6 is a graph showing the effect of the compound of Example 18 in a mouse partial sciatic nerve ligation model (oral administration).
Figure 7:
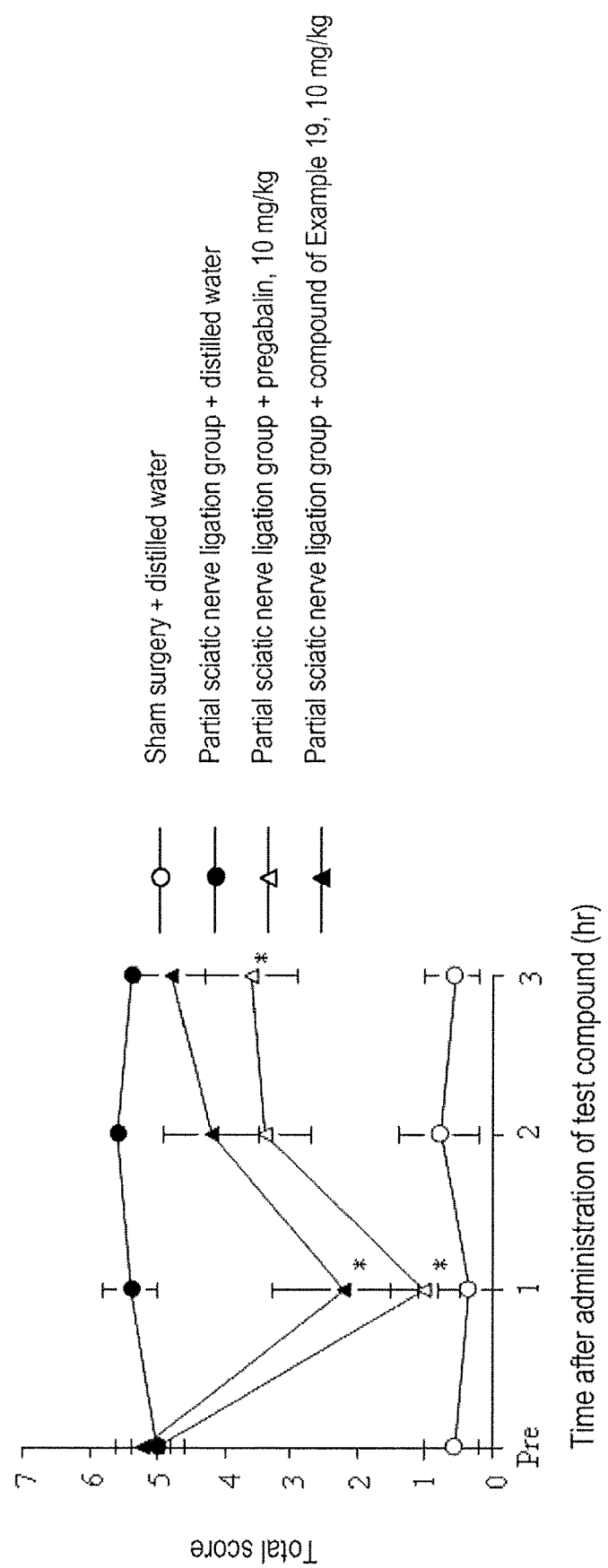
FIG. 7 is a graph showing the effect of the compound of Example 19 in a mouse partial sciatic nerve ligation model (oral administration).
Figure 8:
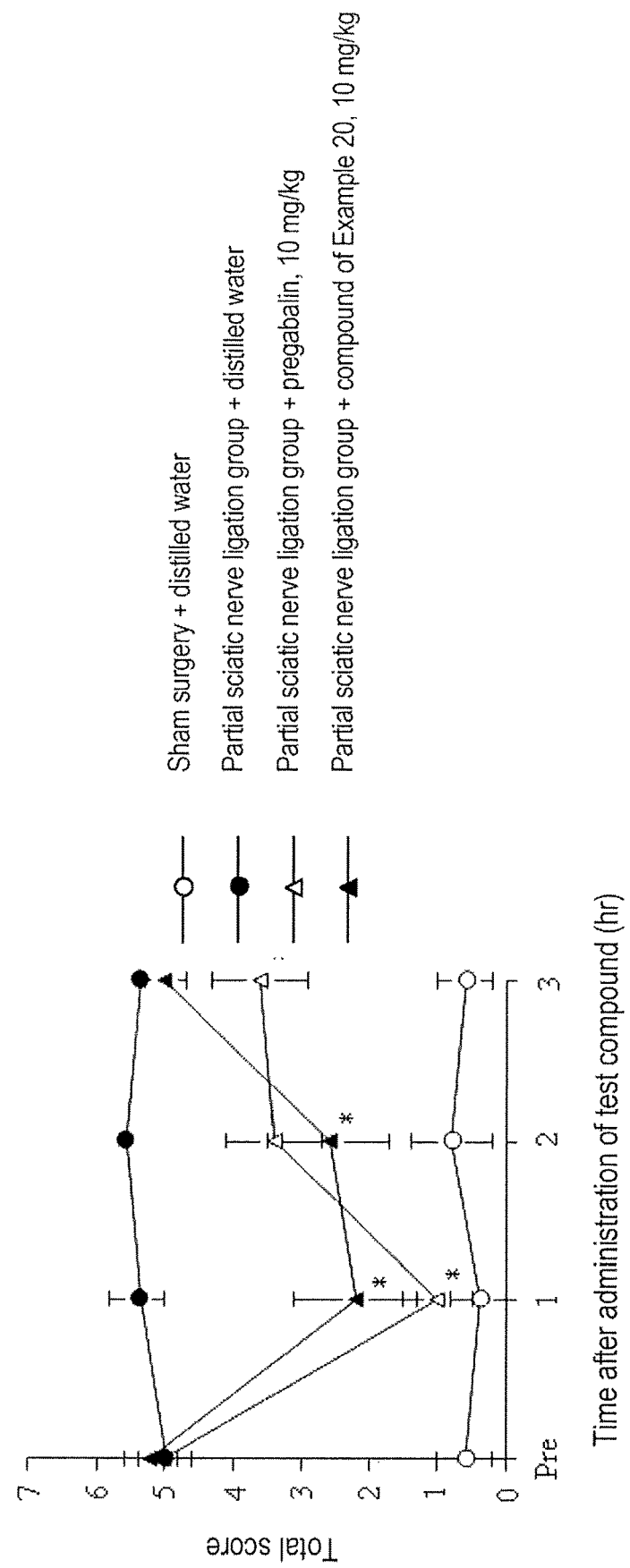
FIG. 8 is a graph showing the effect of the compound of Example 20 in a mouse partial sciatic nerve ligation model (oral administration).
Figure 9:
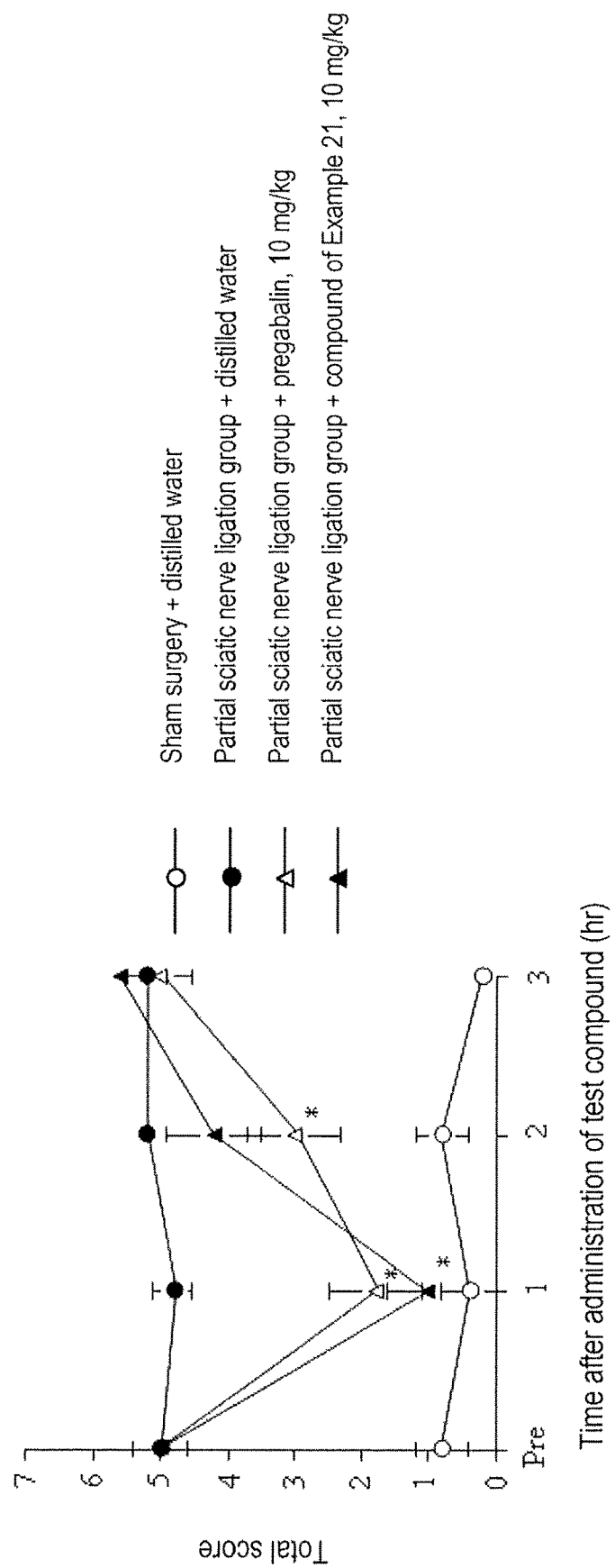
FIG. 9 is a graph showing the effect of the compound of Example 21 in a mouse partial sciatic nerve ligation model (oral administration).
Figure 10:
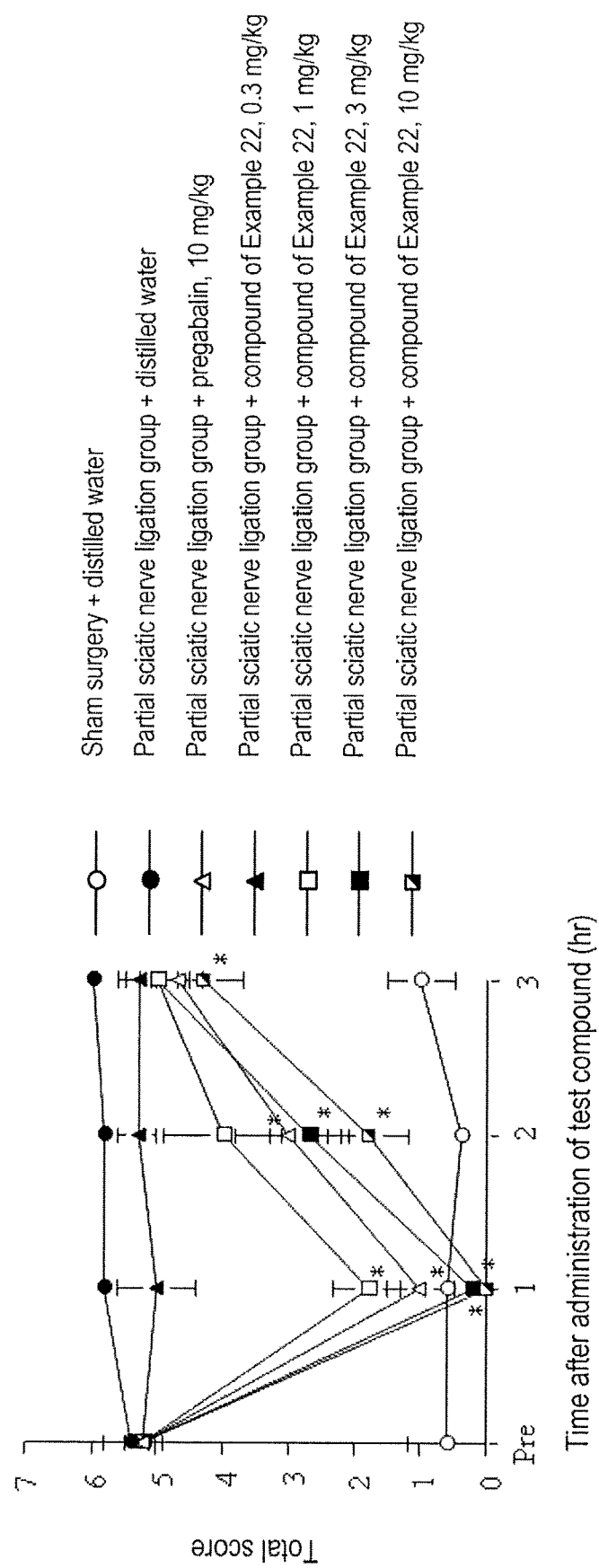
FIG. 10 is a graph showing the effect of the compound of Example 22 in a mouse partial sciatic nerve ligation model (oral administration).
Figure 11:
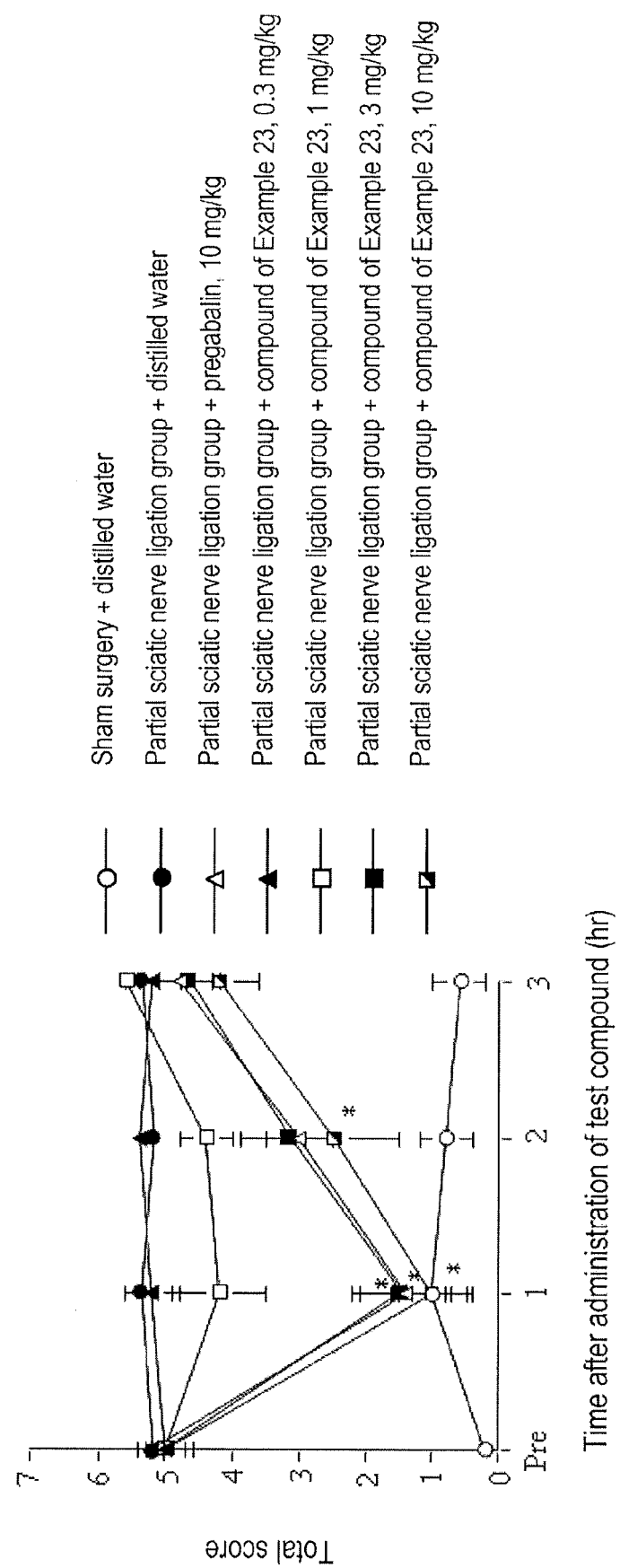
FIG. 11 is a graph showing the effect of the compound of Example 23 in a mouse partial sciatic nerve ligation model (oral administration).
Figure 12:
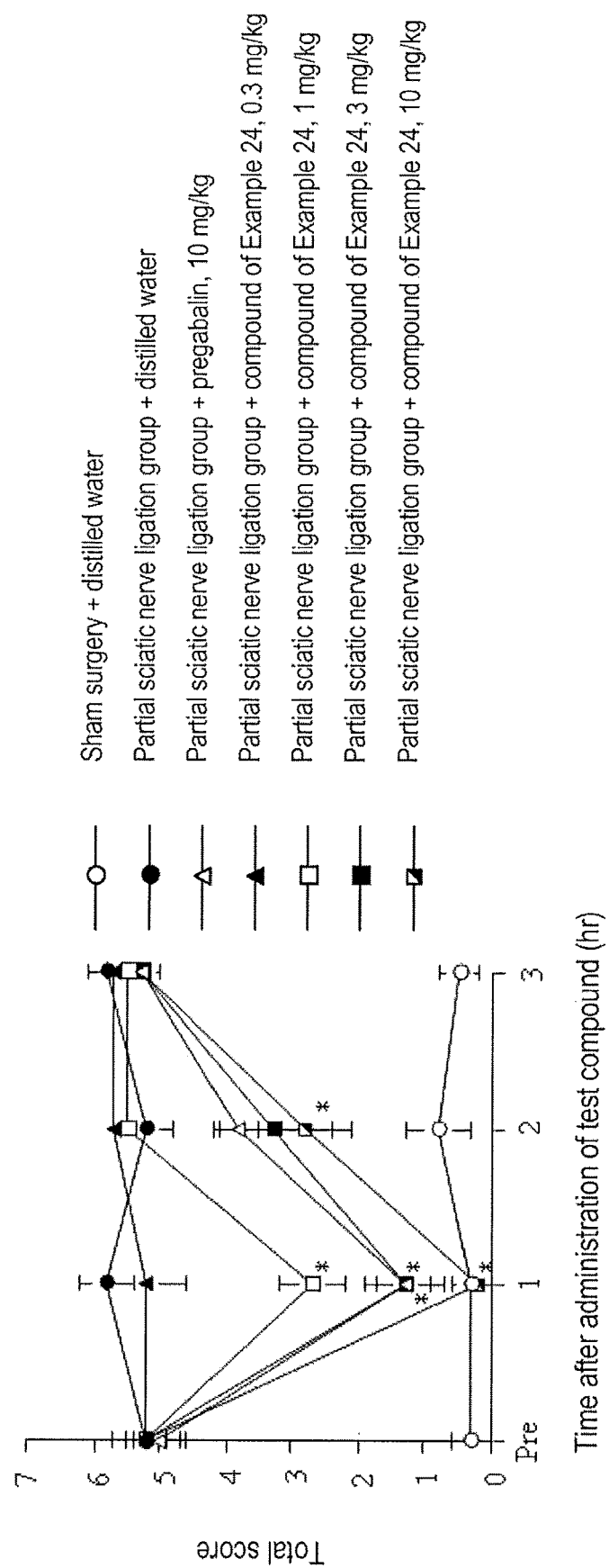
FIG. 12 is a graph showing the effect of the compound of Example 24 in a mouse partial sciatic nerve ligation model (oral administration).

The results are shown in FIGS. 1 to 12. In the figures, the vertical axis represents the total score (mean value±standard error; n=4 to 6 in FIGS. 1 to 12) in the von Frey test. The higher numerical value indicates stronger pain. The horizontal axis represents time (hr) after administration of a test compound. Efficacy was statistically evaluated by a multi-sample unpaired t-test (corrected by Dunnett)(FIGS. 1 to 3 and 10 to 12) or a two-sample unpaired t-test (FIGS. 4 to 9) using the "partial sciatic nerve ligation+distilled water" group ("partial sciatic nerve ligation+distilled water" in the figures) of every measurement time as a control. In the figures, mark "*" indicates that the value is statistically significant (p<0.05) compared to the "partial sciatic nerve ligation+distilled water" group.

According to the results of the von Frey test, oral administration of the compound of Example 13 to 24 ("partial sciatic nerve ligation+the compound of Example 13 to 24" in the figures) showed a statistically significant analgesic action similarly to the positive control, pregabalin ("partial sciatic nerve ligation+pregabalin" in the figures).

From these results, it was clearly demonstrated that a cyclic amine derivative (I) or a pharmacologically acceptable salt thereof has a strong analgesic effect on neuropathic pain.

INDUSTRIAL APPLICABILITY

Our cyclic amine derivative or a pharmacologically acceptable salt thereof can be used as medicines for pain symptoms since it can exhibit an analgesic action against pain, in particular, neuropathic pain.

The invention claimed is:

1. A cyclic amine compound represented by a general formula (I) or a pharmacologically acceptable salt thereof:

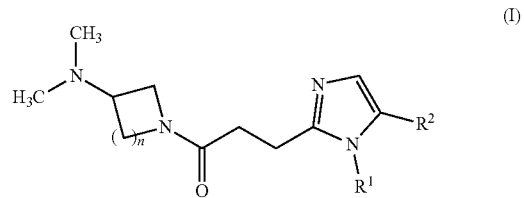

(I)

wherein n represents 1 or 3, $R^1$ represents an alkyl group having 1 to 6 carbon atoms unsubstituted, substituted with one or more halogen atoms or substituted with an alkyloxy group having 1 to 4 carbon atoms and $R^2$ represents a hydrogen atom or a halogen atom.

2. The cyclic amine compound or the pharmacologically acceptable salt thereof according to claim 1, wherein $R^2$ is a hydrogen atom or a chlorine atom.

3. The cyclic amine compound or the pharmacologically acceptable salt thereof according to claim 2, wherein $R^1$ is an unsubstituted alkyl group having 1 to 6 carbon atoms.

4. A medicine comprising the cyclic amine compound or the pharmacologically acceptable salt thereof according to claim 1 as an active ingredient, and a pharmacologically acceptable excipient.

5. An analgesic agent comprising the cyclic amine compound or the pharmacologically acceptable salt thereof according to claim 1 as an active ingredient, and a pharmacologically acceptable excipient.

6. A therapeutic agent for neuropathic pain comprising the cyclic amine compound or the pharmacologically acceptable salt thereof according to claim 1 as an active ingredient, and a pharmacologically acceptable excipient.

7. A medicine comprising the cyclic amine compound or the pharmacologically acceptable salt thereof according to claim 2 as an active ingredient, and a pharmacologically acceptable excipient.

8. A medicine comprising the cyclic amine compound or the pharmacologically acceptable salt thereof according to claim 3 as an active ingredient, and a pharmacologically acceptable excipient.

9. An analgesic agent comprising the cyclic amine compound or the pharmacologically acceptable salt thereof according to claim 2 as an active ingredient, and a pharmacologically acceptable excipient.

10. An analgesic agent comprising the cyclic amine compound or the pharmacologically acceptable salt thereof according to claim 3 as an active ingredient, and a pharmacologically acceptable excipient.

11. A therapeutic agent for neuropathic pain comprising the cyclic amine compound or the pharmacologically acceptable salt thereof according to claim 2 as an active ingredient, and a pharmacologically acceptable excipient.

12. A therapeutic agent for neuropathic pain comprising the cyclic amine compound or the pharmacologically acceptable salt thereof according to claim 3 as an active ingredient, and a pharmacologically acceptable excipient.

13. A method for treating neuropathic pain comprising administering a therapeutically effective amount of the cyclic amine compound or the pharmacologically acceptable salt thereof according to claim 1 to a patient in need thereof.

* * * * *